United States Patent
Gendelman et al.

(10) Patent No.: US 11,839,623 B2
(45) Date of Patent: Dec. 12, 2023

(54) ANTIVIRAL PRODRUGS AND FORMULATIONS THEREOF

(71) Applicant: BOARD OF REGENTS OF THE UNIVERSITY OF NEBRASKA, Lincoln, NE (US)

(72) Inventors: Howard E. Gendelman, Omaha, NE (US); Benson Edagwa, Omaha, NE (US)

(73) Assignee: BOARD OF REGENTS OF THE UNIVERSITY OF NEBRASKA, Lincoln, NE (US)

( * ) Notice: Subject to any disclaimer, the term of this patent is extended or adjusted under 35 U.S.C. 154(b) by 110 days.

(21) Appl. No.: 16/772,995

(22) PCT Filed: Jan. 14, 2019

(86) PCT No.: PCT/US2019/013462
§ 371 (c)(1),
(2) Date: Jun. 15, 2020

(87) PCT Pub. No.: WO2019/140365
PCT Pub. Date: Jul. 18, 2019

(65) Prior Publication Data
US 2020/0390796 A1    Dec. 17, 2020

Related U.S. Application Data

(60) Provisional application No. 62/616,549, filed on Jan. 12, 2018.

(51) Int. Cl.
| A61K 31/7076 | (2006.01) |
| A61P 31/18 | (2006.01) |
| A61K 9/51 | (2006.01) |
| A61K 31/7068 | (2006.01) |

(52) U.S. Cl.
CPC ........ *A61K 31/7076* (2013.01); *A61K 9/5146* (2013.01); *A61K 31/7068* (2013.01); *A61P 31/18* (2018.01)

(58) Field of Classification Search
CPC .. A61K 31/7076; A61K 31/7068; A61P 31/18
See application file for complete search history.

(56) References Cited

U.S. PATENT DOCUMENTS

| | | |
|---|---|---|
| 5,145,684 A | 9/1992 | Liversidge et al. |
| 6,045,829 A | 4/2000 | Liversidge et al. |
| 6,068,858 A | 5/2000 | Liversidge et al. |
| 6,835,396 B2 | 12/2004 | Brynjelsen et al. |
| 7,112,340 B2 | 9/2006 | Kipp et al. |
| 9,808,428 B2 | 11/2017 | Gendelman et al. |
| 11,311,545 B2 | 4/2022 | Gendelman et al. |
| 11,458,136 B2 | 10/2022 | Gendelman et al. |
| 2002/0041898 A1 | 4/2002 | Unger et al. |
| 2004/0138157 A1 | 7/2004 | Walker |
| 2005/0048002 A1 | 3/2005 | Rabinow et al. |
| 2006/0280430 A1 | 12/2006 | Rabinow et al. |
| 2007/0003608 A1 | 1/2007 | Almond et al. |
| 2007/0042988 A1 | 2/2007 | Klumpp et al. |
| 2008/0241256 A1 | 10/2008 | Kuhn |
| 2009/0274765 A1 | 11/2009 | Beduneau et al. |
| 2011/0039798 A1 | 2/2011 | Doncel et al. |
| 2011/0085987 A1 | 4/2011 | Wang et al. |
| 2012/0202823 A1 | 8/2012 | Zeidan et al. |
| 2013/0236553 A1 | 9/2013 | Gendelman et al. |
| 2013/0244966 A1 | 9/2013 | Milne et al. |
| 2014/0017330 A1 | 1/2014 | Vinogradov |
| 2014/0099283 A1 | 4/2014 | Gosselin et al. |
| 2014/0323425 A1 | 10/2014 | Calvez et al. |
| 2015/0297587 A1 | 10/2015 | Gelbard et al. |
| 2017/0304308 A1 | 10/2017 | Gendelman et al. |
| 2021/0113558 A1 | 4/2021 | Gendelman et al. |
| 2022/0211714 A1 | 7/2022 | Gendelman et al. |

FOREIGN PATENT DOCUMENTS

| | | | |
|---|---|---|---|
| EP | 0349242 A2 | 1/1990 | |
| EP | 2682397 A1 * | 1/2014 | ............... A61P 1/16 |
| JP | H04295420 A | 10/1992 | |
| WO | WO-9902665 A1 | 1/1999 | |
| WO | WO-2000066090 A1 | 11/2000 | |
| WO | WO-02087424 A2 | 11/2002 | |
| WO | WO-2004069812 A1 | 8/2004 | |
| WO | WO-2005072706 A2 | 8/2005 | |
| WO | WO-2006116764 A1 | 11/2006 | |
| WO | WO-2007095269 A2 | 8/2007 | |
| WO | WO-2009051837 A2 | 4/2009 | |
| WO | WO-2010009075 A1 | 1/2010 | |
| WO | WO-2010011814 A1 | 1/2010 | |
| WO | WO-2011119566 A1 | 9/2011 | |
| WO | WO-2012037320 A2 | 3/2012 | |
| WO | WO-2012061480 A2 | 5/2012 | |
| WO | WO-20120158811 A2 | 11/2012 | |
| WO | WO-2013158549 A1 | 10/2013 | |
| WO | WO-2014085795 A1 | 6/2014 | |
| WO | WO-2014169207 A1 | 10/2014 | |
| WO | WO-2015108945 A2 | 7/2015 | |
| WO | WO-2015127437 A1 | 8/2015 | |
| WO | WO-2016057866 A1 | 4/2016 | |
| WO | WO-2016099982 A2 | 6/2016 | |
| WO | WO-20170223280 A2 | 12/2017 | |
| WO | WO-20190140365 A1 | 7/2019 | |
| WO | WO-2019199756 A1 | 10/2019 | |

OTHER PUBLICATIONS

Huang, B., et al., First discovery of a potential carbonate prodrug of NNRTI drug candidate RDEA427 with submicromolar inhibitory activity against HIV-1 K103N/Y181C double mutant strain, Bioorg Med Chem Lett, 28(8): 1348-1351 (2018).

Irby, D., et al., Lipid-drug conjugate for enhancing drug delivery, Mol Pharm, 14(5): 1325-1338 (2017).

Namasivayam, V., et al., The Journey of HIV-1 non-nucleoside reverse transcriptase inhibitors (NNRTIs) from lab to clinic, J Med Chem, 62(10): 4851-4883 (2019).

PCT/US2015/054826 International Search Report and Written Opinion dated Jan. 7, 2016.

(Continued)

*Primary Examiner* — Andrew S Rosenthal
(74) *Attorney, Agent, or Firm* — White & Case LLP

(57) ABSTRACT

The present invention provides prodrugs and methods of use thereof.

18 Claims, 18 Drawing Sheets

(56) References Cited

OTHER PUBLICATIONS

Figure 1A:
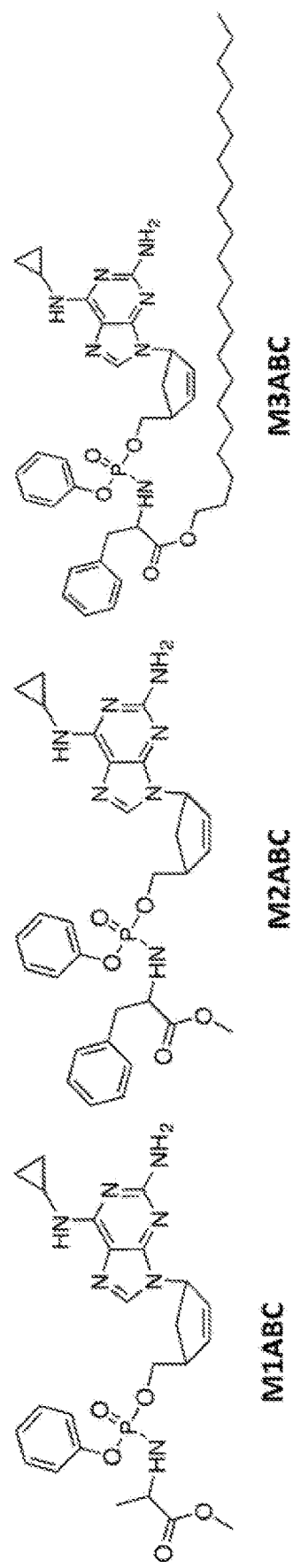

PCT/US2019/026497 International Search Report and Written Opinion dated Jun. 18, 2019.
Rohde, M., et al., Biological conversion of aripiprazole lauroxil—An N-acyloxymethyl aripiprazole prodrug, Results Pharma Sci, 4: 19-25 (2014).
Agarwal, A.G., et al., Synthesis and biological evaluation of fatty acyl ester derivatives of (-)-2',3'- dideoxy-3'-thiacytidine, J Med Chem, 55(10): 4861-4871 (2012).
Arainga, M., et al., Opposing regulation of endolysosomal pathways by long-acting nanoformulated antiretroviral therapy and HIV-1 in human macrophages, Retrovirology, 12: 5 (2015).
Baert, L., et al., Development of a long-acting injectable formulation with nanoparticles of rilpivirine (TMC278) for HIV treatment, Eur J Pharm Biopharm, 72(3): 502-508 (2009).
Balkundi, S., et al., Comparative manufacture and cell-based delivery of antiretroviral nanoformulations, Int J Nanomedicine, 6: 3393-3404 (2011).
Batrakova, E.V., et al., Cell-mediated drugs delivery, Expert Opin Drug Deliv, 8(4): 415-433 (2011).
Bhatia, M., et al., Nanoparticle technology for the delivery of poorly water-soluble drug, Pharm Tech, 30(2): 82-92 (2006).
Chattopadhyay, N., et al., Solid lipid nanoparticles enhance the delivery of the HIV protease inhibitor, atazanavir, by a human brain endothelial cell line, Pharm Res, 25(10): 2262-2271 (2008).
Dobrowska-Mas, E., Insights on fatty acids in lipophlic prodrug strategy, IRJPAC, 14(4): 1-10 (2017).
Edagwa, B.J., et al., Development of HIV reservoir targeted long acting nanoformulated antiretroviral therapies, Curr Med Chem, 21(36): 4186-4198 (2014).
Edagwa, B.J., et al., Long-acting antituberculous therapeutic nanoparticles target macrophage endosomes, FASEB J, 28(12): 5071-5082 (2014).
Gautam, N., et al., Pharmacokinetics, biodistribution, and toxicity of folic acid-coated antiretroviral nanoformulations, Antimicrob Agents Chemother, 58(12): 7510-7519 (2014).
Gautam, N., et al., Preclinical pharmacokinetics and tissue distribution of long-acting nanoformulated antiretroviral therapy, Antimicrob Agents Chemother, 57(7): 3110-3120 (2013).
Gavegnano, C., et al., Antiretroviral therapy in macrophages: implication for HIV eradication. Antivir Chem Chemother, 20(2): 63-78 (2009).
Guarino, V.R., et al., Prodrugs of amides, imides and other NH-acidic compounds in Prodrugs: Challenges and Rewards Part 1, p. 24, American Association of Pharmaceutical Sciences, New York, pp. 134-187 (2007).
Guo, D., et al., Creation of a long-acting nanoformulated 2',3'-dideoxy-3'-thiacytidine, J Acquir Immune Defic Syndr, 74(3): e75-e83 (2017).
Guo, D., et al., Endosomal trafficking of nanoformulated antiretroviral therapy facilitates drug particle carriage and HIV clearance, J Virol, 88(17): 9504-9513 (2014).
Jain, S.K., et al., Mannosylated gelatin nanoparticles bearing an anti-HIV drug didanosine for site-specific delivery, Nanomedicine, 4(1): 41-48 (2008).
Kanmogne, G.D., et al., Mononuclear phagocyte intercellular crosstalk facilitates transmission of cell-targeted nanoformulated atiretroviral drugs to human brain endothelial cells, Int J Nanomedicine, 7: 2373-2388 (2012).
Kinman, L., et al., Optimization of lipid-indinavir complexes for localization in lymphoid tissues of HIV-infected macaques, J Acquir Immune Defic Sundr, 42(2): 155-161 (2006).
Krise, J.P., et al., Prodrugs of Amines in Prodrugs: Challenges and Rewards Part 1, American Association of Pharmaceutical Sciences, New York, pp. 102-131 (2007).
Law, D., et al., Physicochemical considerations in the preparation of amorphous ritonavir-poly (ethylene glycol) 8000 solid dispersions, J Pharm Sci, 90(8): 1015-1025 (2001).
Li, Q., et al., Synthesis of lamivudine stearate and antiviral activity of stearic acid-g-chitosan oligosaccharide polymeric micelles delivery system, Eur J Pharm Sci, 41(3-4): 498-507 (2010).
Lin, Z., et al., ProTide generated long-acting abacavir nanoformulations, Chem Commun (Cambridge), 54(60): 8371-8374 (2018).
Liu, F., et al., Targeted cancer therapy with novel high drug-loading nanocrystals, J Pharm Sci, 99(8): 3542-3551 (2010).
Low, P.S., et al., Discovery and development of folic-acid-based receptor targeting for imaging and therapy of cancer and inflammatory diseases, Acc Chem Res, 41(1): 120-129 (2008).
McGuigan, C., et al., The application of phosphoramidate ProTide technology to the potent anti- HCV compound 4'-azidocytidine (R1479), Bioorg Med Chem Lett, 19(15): 4250-4254 (2009).
Moghimi, S.M., et al., Poloxamers and poloxamines in nanoparticle engineering and experimental medicine, Trends Biotechnol, 18(10): 412-420 (2000).
Nowacek, A.S., Development of a macrophage-mediated delivery system for crystalline antiretroviral nanoparticles, Dissertation, University of Nebraska, 219 pages (2011).
Nowacek, A.S., et al., NanoART synthesis, characterization, uptake, release and toxicology for human monocyte-macrophage drug delivery, Nanomedicine (Lond.), 4(8): 903-917 (2009).
Nowacek, A.S., et al., Nanoformulated antiretroviral Combinations extend drug release and antiretroviral responses in HIV-1 infected macrophages: Implications for neuroAIDS therapeutics, J Neuroimmune Pharmacol, 5(4): 592-601 (2010).
PCT/US2019/013462 International Search Report and Written Opinion dated Mar. 5, 2019.
Puligujja, P., et al., Macrophage Folate Receptor-Targeted Antiretroviral Therapy Facilitates Drug Entry, Retention, Antiretroviral Activities and Biodistribution for Reduction of Human Immunodeficiency Virus Infections, Nanomedicine, 9(8): 1263-1273 (2013).
Puligujja, P., et al., Pharmacodynamics of long-acting folic acid-receptor targeted ritonavir-boosted atazanavir nanoformulations, Biomaterials, 41: 141-150 (2015).
Rowe, R.C., et al., Handbook of Pharmaceutical Excipients, 6th Edition, Pharmaceutical Press, pp. 317-324 (2009).
The essential chemical industry—online, pp. 1-8, (2013) retrieved on Feb. 8, 2018 from,http://www.essentialchemical industry.ord/materials-and-applications/surfactants.html.
The Merck Index Online entries for "Atazanavir" (monograph M2119), "Idinavir" (monograph M6253), and "Ritonavir" (monograph M9636), 5 pages (2013).
Thomas, T.P., et al., Folate-targeted nanoparticles show efficacy in the treatment of inflammatory arthritis, Arthritis Rheum, 63(9): 2671-2680 (2011).
Xia, W., et al., A functional folate receptor is induced during macrophage activation and can be used to target drugs to activated macrophages, Blood, 113(2): 438-446 (2009).
Cobb, D.A., et al., Transformation of tenofovir into stable ProTide nanocrystals with long-acting pharmacokinetic profiles, Nat Commun, 12(1): 5458 (2021).
Elworthy, T.R., et al., Orally bioavailable prodrugs of a BCS class 2 molecule, an inhibitor of HIV-1 reverse transcriptase, Bioorg Med Chem Lett. 18(24): 6344-6347 (2008).
PCT/US2017/038693 International Search Report and Written Opinion dated Nov. 27, 2017.

* cited by examiner

Step 1: Synthesis of amino acid esters

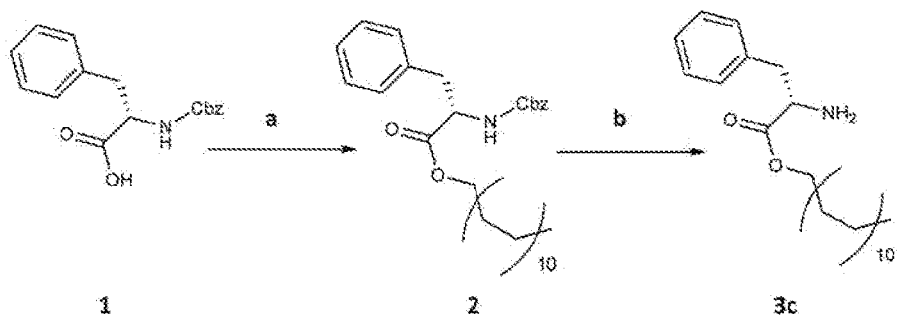

Step 2: Synthesis of aryl aminoacyl phosphorochloridates.

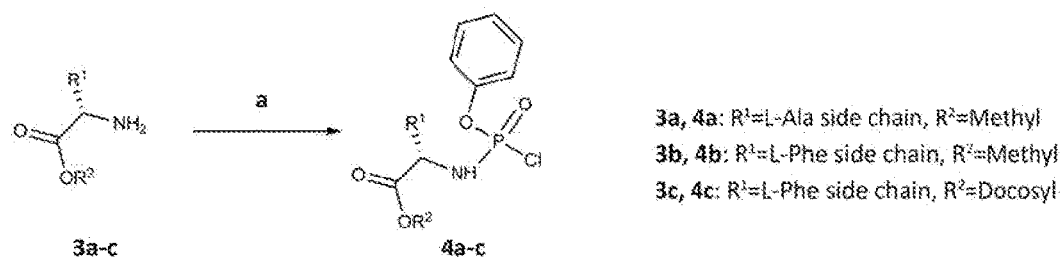

3a, 4a: R¹=L-Ala side chain, R²=Methyl
3b, 4b: R¹=L-Phe side chain, R²=Methyl
3c, 4c: R¹=L-Phe side chain, R²=Docosyl

Step 3. Synthesis of Abacavir ProTides under coupling conditions.

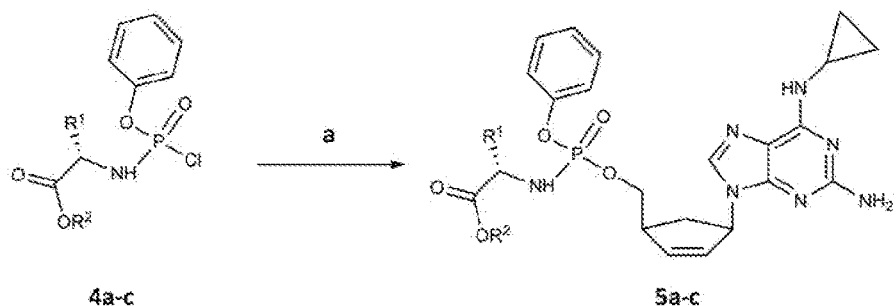

M1ABC (5a): R¹=L-Ala side chain, R²=Methyl
M2ABC (5b): R¹=L-Phe side chain, R²=Methyl
M3ABC (5c): R¹=L-Phe side chain, R²=Docosyl

FIG. 1E

ANTIVIRAL PRODRUGS AND FORMULATIONS THEREOF

This application is a § 371 application of PCT/US2019/013462, filed Jan. 14, 2019, which claims priority under 35 U.S.C. § 119(e) to U.S. Provisional Patent Application No. 62/616,549, filed Jan. 12, 2018. The foregoing application is incorporated by reference herein.

This invention was made with government support under Grants Nos. P01DA028555, R01AG043540, R01NS034239, R01NS036126, P01MH064570, P01NS043985, and P30MH062261 awarded by the National Institutes of Health. The government has certain rights in the invention.

FIELD OF THE INVENTION

The present invention relates generally to the delivery of therapeutics. More specifically, the present invention relates to compositions and methods for the delivery of therapeutic agents to a patient for the treatment of a disease or disorder.

BACKGROUND OF THE INVENTION

Nucleoside analogs and their prodrug derivatives have been used to manage viral infections and cancers for decades (De Clercq, et al., Clin. Microbiol. Rev. (2016) 29:695-747; Shelton, et al., Chem. Rev. (2016) 116:14379-14455). They are particularly important in the treatment and prevention of human immunodeficiency virus (HIV) infections (e.g., lamivudine, abacavir, emtricitabine, tenofovir, tenofovir alafenamide, and tenofovir disoproxil fumarate); herpes virus (HSV) infections (e.g., acyclovir, valacyclovir, ganciclovir, valganciclovir, penciclovir, famciclovir, brivudine, and cidofovir); hepatitis B (HBV) and hepatitis C (HCV) viruses (e.g., sofosbuvir, adefovir dipivoxil and ribavirin); influenza virus (e.g., laninamivir). Nucleoside analogs and their prodrug derivatives such as capecitabine, cytarabine and gemcitabine have also been effectively used in cancer chemotherapy. Nucleoside analogs and their prodrug derivatives such as ticagrelor have also been effectively used as antiplatelet drugs.

However, nucleoside analogs require host or viral kinase mediated conversion into their therapeutically active triphosphate forms prior to incorporation into elongating DNA or RNA, causing chain termination. Catalytic phosphorylation efficiency of synthetic nucleosides is slow and inefficient. Therefore, preactivated nucleosides as monophosphates have been utilized (McGuigan, et al., AIDS (1991) 5:1536-7; Mehellou, et al., J. Med. Chem. (2018) 61(6): 2211-2226). However, few monophosphate based nucleoside prodrugs have been approved by the U.S. Food and Drug Administration for treatment and prevention of HIV, HBV, and HCV infections.

There are few pharmacological approaches to improve delivery of phosphorylated antiviral and antitumor agents (Mehellou, et al., J. Med. Chem. (2018) 61(6):2211-2226). Conventional nucleoside administrations have numerous limitations such as variable drug pharmacokinetic profiles, limited cellular and tissue penetration, and systemic toxicities. Many of these hurdles stem from intrinsic poor physicochemical properties of the parent drugs and their prodrug derivatives. Frequent high doses are often needed to maintain therapeutically effective drug concentrations in restricted disease sanctuaries. Challenges in identification and synthesis of non-toxic pharmaceutically active agents have frustrated efforts to improve biodistribution and extend drug half-lives. Additionally, currently available treatment regimens suffer from short drug half-lives underscoring the need for long acting with slow, effective release nanoformulations to affect drug carriage into restricted anatomical reservoirs of infection. Accordingly, there is a need for drug delivery systems that improve intracellular delivery of preactivated nucleosides.

SUMMARY OF THE INVENTION

In accordance with the instant invention, prodrugs of a nucleoside, a nucleotide, or a nucleobase analog are provided. In a particular embodiment, the prodrug comprises a nucleoside, a nucleotide, or a nucleobase analog conjugated to a monophosphonate or phosphoramidate, wherein one or more of the —OH groups of the monophosphonate or phosphoramidate group is replaced with an O-aryl group and/or an amino acid, and wherein the prodrug comprises an ester comprising an aliphatic or alkyl group (e.g., an aliphatic or alkyl comprising about 3 to about 30 carbons). In a particular embodiment, the prodrug is a compound having a formula selected from one of Formulas (I)-(X) or a pharmaceutically acceptable salt thereof, wherein X is a nucleoside, nucleotide, or nucleobase analog; $R_1$ is an aliphatic or alkyl group; $R_2$ is hydrogen, alkyl group, or aryl group; $R_3$ is an optionally substituted aryl group; and $R_4$ is an alkyl group, substituted carbon atom, or a heteroatom. In a particular embodiment, the prodrug is a compound of Formula (I) or a pharmaceutically acceptable salt thereof. In a particular embodiment, X is a nucleoside analog such as a nucleoside analog reverse transcriptase inhibitor (NRTI). In a particular embodiment, $R_1$ is the alkyl chain of a fatty acid or a C13-C24 unsaturated or saturated alkyl or aliphatic group, optionally substituted with at least one heteroatom. In a particular embodiment, $R_2$ is any D or L amino acid side chain (e.g., H, phenyl, $CH_3$, —$CH_2$iPr, —$CH_2$Ph, or —$CH_2$PhOH). In a particular embodiment, $R_3$ is phenyl or naphthyl. In a particular embodiment, $R_4$ is $CH_2$ or a heteroatom. In a particular embodiment, the nucleoside, nucleotide, or nucleobase analog comprises an analog selected from the group consisting of abacavir (ABC), tenofovir, tenofovir alafenamide (TAF), tenofovir disoproxil fumarate, lamivudine (3TC), emtricitabine (FTC), didanosine, vidarabine, BCX4430, cytarabine, gemcitabine, zalcitabine, entecavir, acyclovir, valacyclovir, ganciclovir, valganciclovir, penciclovir, famciclovir, brivudine, cidofovir, sofosbuvir, adefovir, adefovir dipivoxil, laninamivir, stavudine, telbivudine, zidovudine, ribavirin, idoxuridine, trifluridine, ticagrelor, cangrelor, 5-fluorouracil (5-FU), 5-bromo-2-deoxy-uridine, capecitabine, cladribine, capecitabine, 4'-ethynyl-2-fluoro-2'-deoxyadenosine (EFdA), and fludarabine. Composition comprising at least one prodrug of the instant invention and at least one pharmaceutically acceptable carrier are also encompassed by the present invention.

In accordance with another aspect of the instant invention, nanoparticles comprising at least one prodrug of the instant invention and at least one polymer or surfactant are provided. In a particular embodiment, the prodrug is crystalline. In a particular embodiment, the polymer or surfactant is an amphiphilic block copolymer such as an amphiphilic block copolymer comprising at least one block of poly(oxyethylene) and at least one block of poly(oxypropylene) (e.g., poloxamer 407). The nanoparticle may comprise a polymer or surfactant linked to at least one targeting ligand. An individual nanoparticle may comprise targeted and non-targeted surfactants. In a particular embodiment, the nanoparticles have a diameter of about 100 nm to 1 μm.

Composition comprising at least one nanoparticle of the instant invention and at least one pharmaceutically acceptable carrier are also encompassed by the present invention.

In accordance with another aspect of the instant invention, methods for treating, inhibiting, and/or preventing a disease or disorder in a subject in need thereof are provided. The methods comprise administering to the subject at least one prodrug or nanoparticle of the instant invention, optionally within a composition comprising a pharmaceutically acceptable carrier. In a particular embodiment, the disease or disorder is cancer, viral infection, or a clotting disorder. In a particular embodiment, the viral infection is an HIV, hepatitis B, hepatitis C, influenza A, influenza B, herpes simplex, or Ebola infection. In a particular embodiment, the method further comprises administering at least one further therapeutic agent or therapy for the disease or disorder, e.g., at least one additional anti-HIV compound.

BRIEF DESCRIPTIONS OF THE DRAWING

Figure 1B:
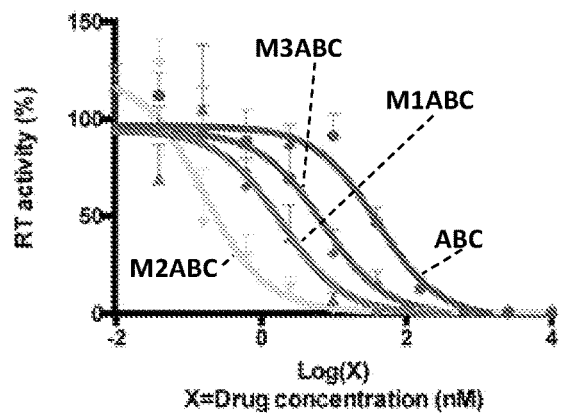
Figure 1C:
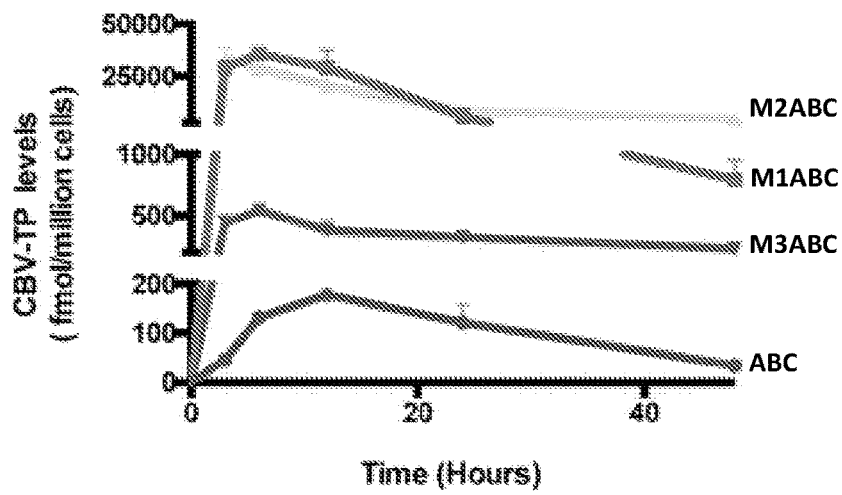
Figure 1D:
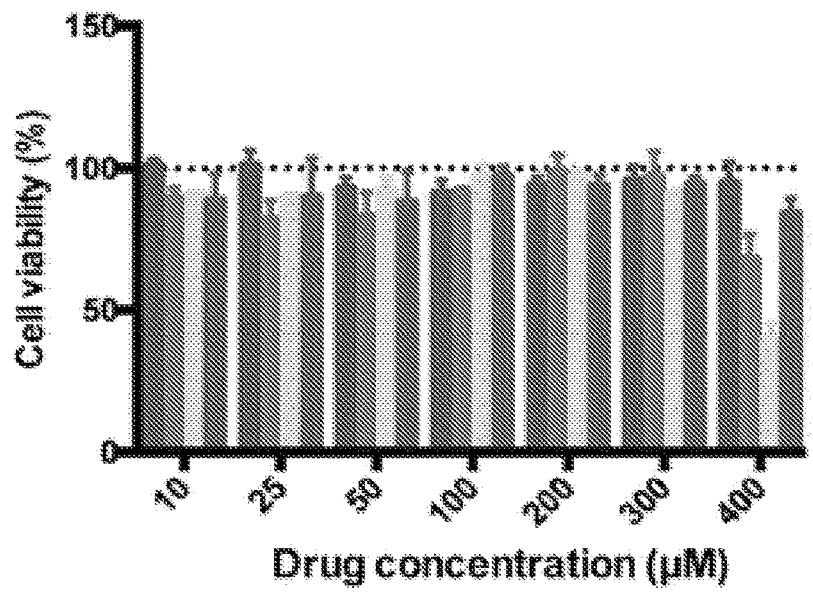
Figure 1F:
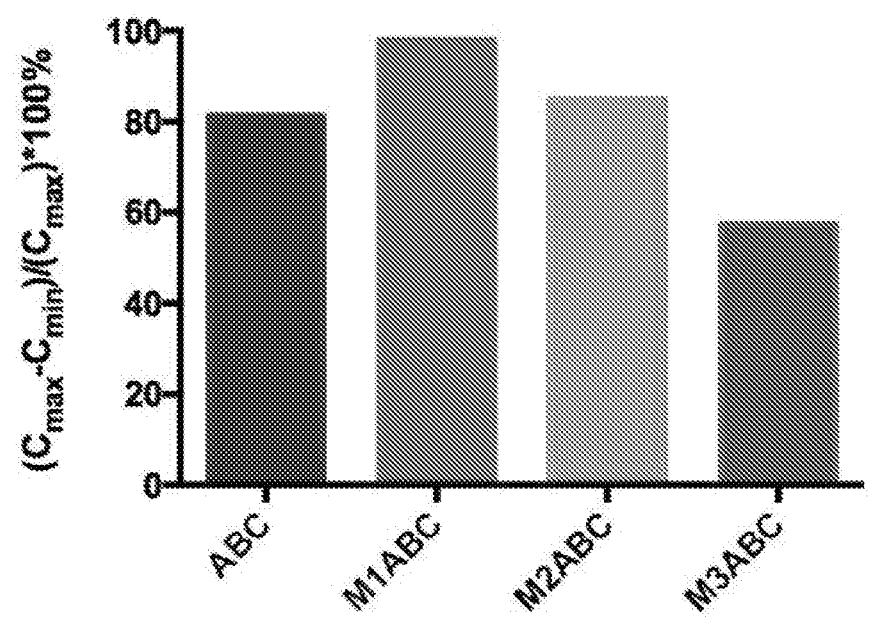

FIG. 1A provides the structure of M1ABC, M2ABC, and M3ABC. FIG. 1B provides a graph of the $EC_{50}$ of abacavir (ABC), M1ABC, M2ABC, and M3ABC against HIV-$1_{ADA}$ determined in monocyte-derived macrophages (MDM). FIG. 1C provides a graph of the intracellular CBV-TP levels measured after MDMs were treated with 10 μM free ABC, M1ABC, M2ABC, or M3ABC for the indicated times. FIG. 1D provides a graph of the cytotoxicity of ABC, M1ABC, M2ABC, and M3ABC in MDMs (provided from left to right for each drug concentration shown). Results are shown as percentage of cell viability as compared to untreated MDMs. Data are presented as mean±standard deviation (SD) for n=3 samples per group. FIG. 1E provides a synthesis scheme for ABC prodrugs. Briefly, Step 1(a): 1-docosanol, HATU, imidazole, $Et_3N$, $DMF/CHCl_3$, 45° C., 48 hours; Step 1(b): Pd/C, $Et_3SiH$, $MeOH/CHCl_3$ (1:1 v/v), room temperature, 16 hours; Step 2(a): phenyl dichlorophosphate, $Et_3N$, $CH_2Cl_2$, −78° C.-room temperature, 16 hours; and Step 3(a): ABC, tert-BuMgCl, THF, −78° C.-room temperature, 48-90 hours. FIG. 1F provides a graph of the rate of decline of intracellular levels of CBV-TP. The percent change was calculated as $(C_{max}−C_{min})/(C_{max})*100$. For ABC, M1ABC, M2ABC, and M3ABC, the percentage decreases were 81.2%, 97.8%, 84.8%, and 57.3% from $C_{max}$, at 48 hours, respectively.

Figure 2A:
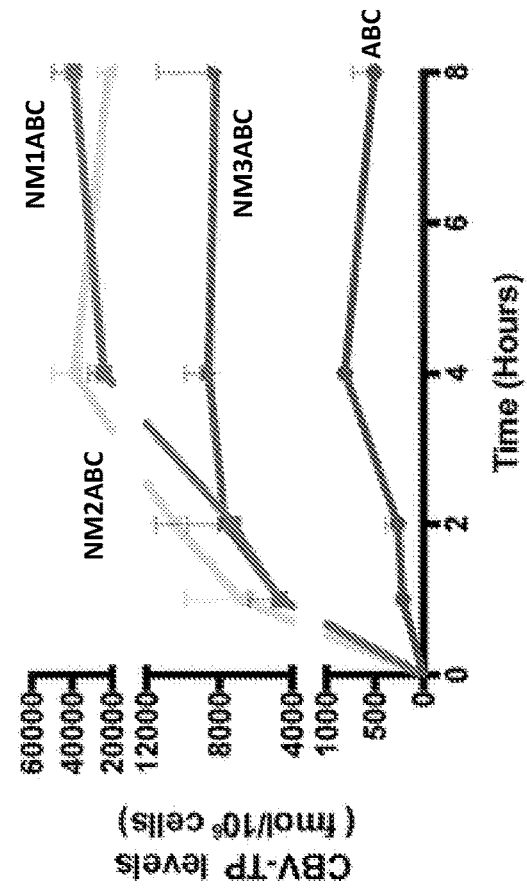
Figure 2C:
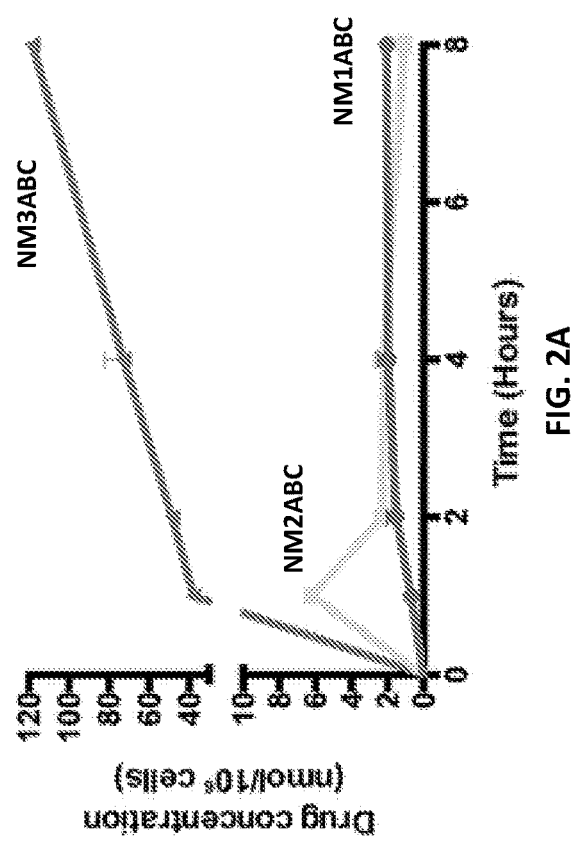
Figure 2B:
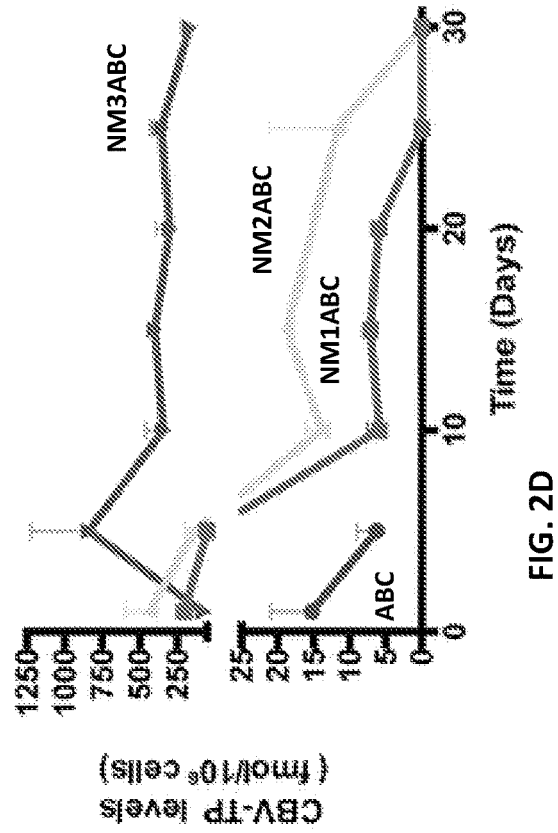
Figure 2D:
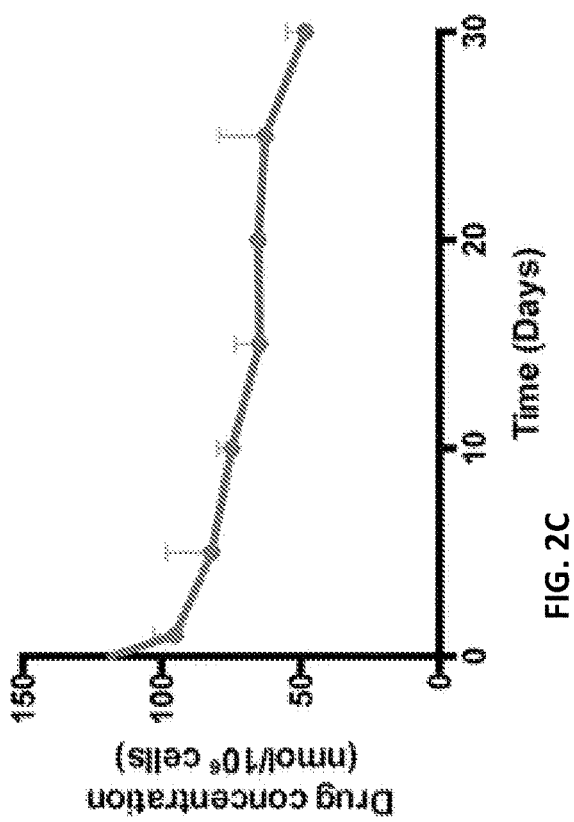
Figure 2E:
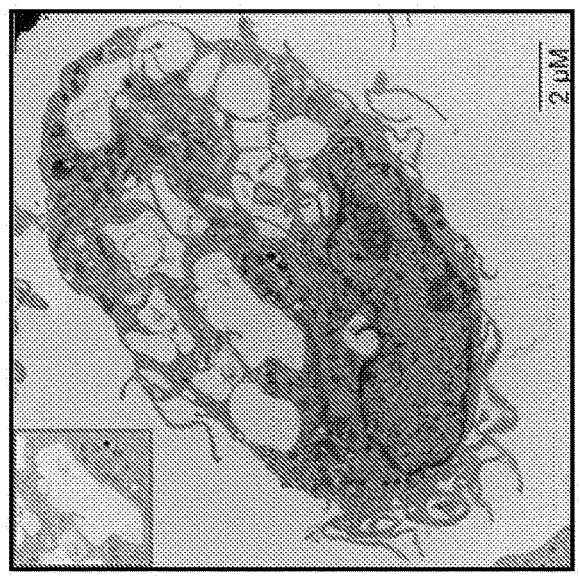
Figure 2E:
Figure 2E:
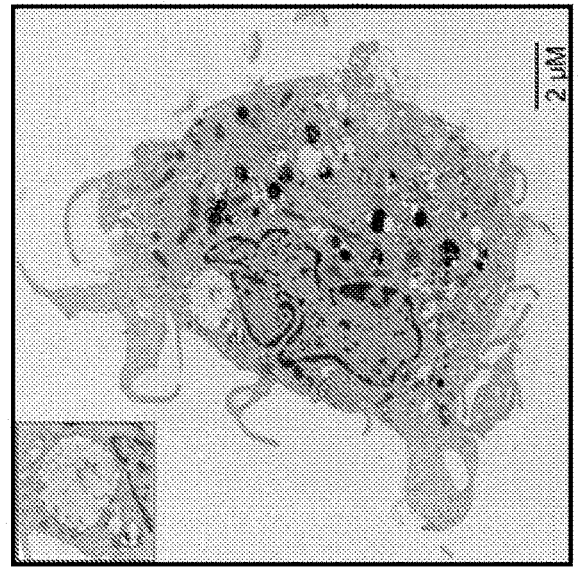

FIG. 2A provides a graph of the intracellular prodrug concentration in MDMs after treatment with 100 μM ABC or prodrug nanoformulations for 1-8 hours. FIG. 2B provides a graph of the intracellular carbovir-triphosphate (CBV-TP) levels measured after MDMs were treated with 100 μM ABC or prodrug nanoformulations for 1-8 hours. FIG. 2C provides a graph of the intracellular prodrug concentration in MDMs after an 8 hour loading with NM3ABC followed by half media exchanges every other day for up to 30 days. FIG. 2D provides a graph of the intracellular CBV-TP levels measured in MDMs after an 8 hour drug loading followed by half media exchanges every other day for up to 30 days. For FIGS. 2A-2D, data are expressed as mean±SD for n=3 samples per group. FIG. 2E provides images of transmission electron microscopy (TEM) to visualize the morphologies of the formulation-loaded MDMs after 8 hours incubation with nanoformulations.

Figure 3B:
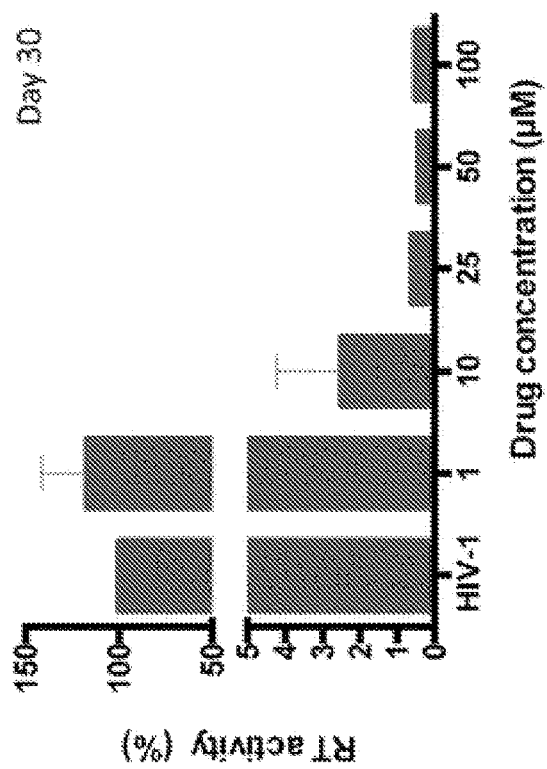
Figure 3A:
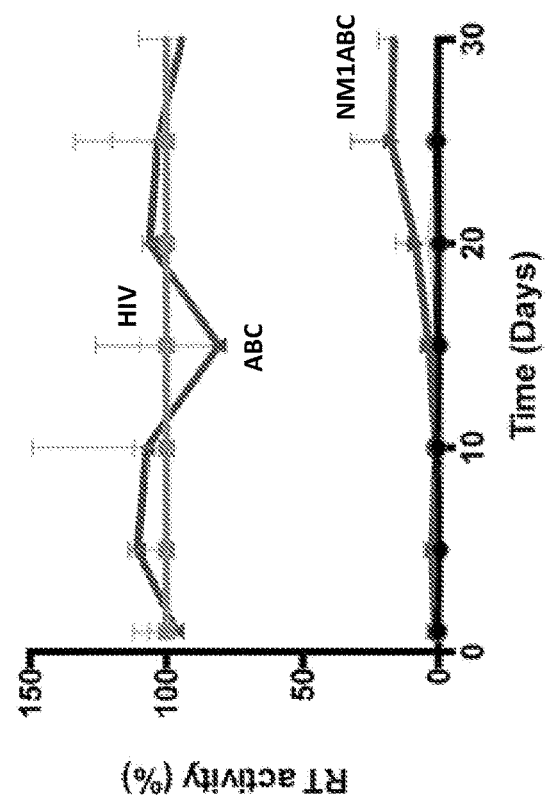
Figure 3C:
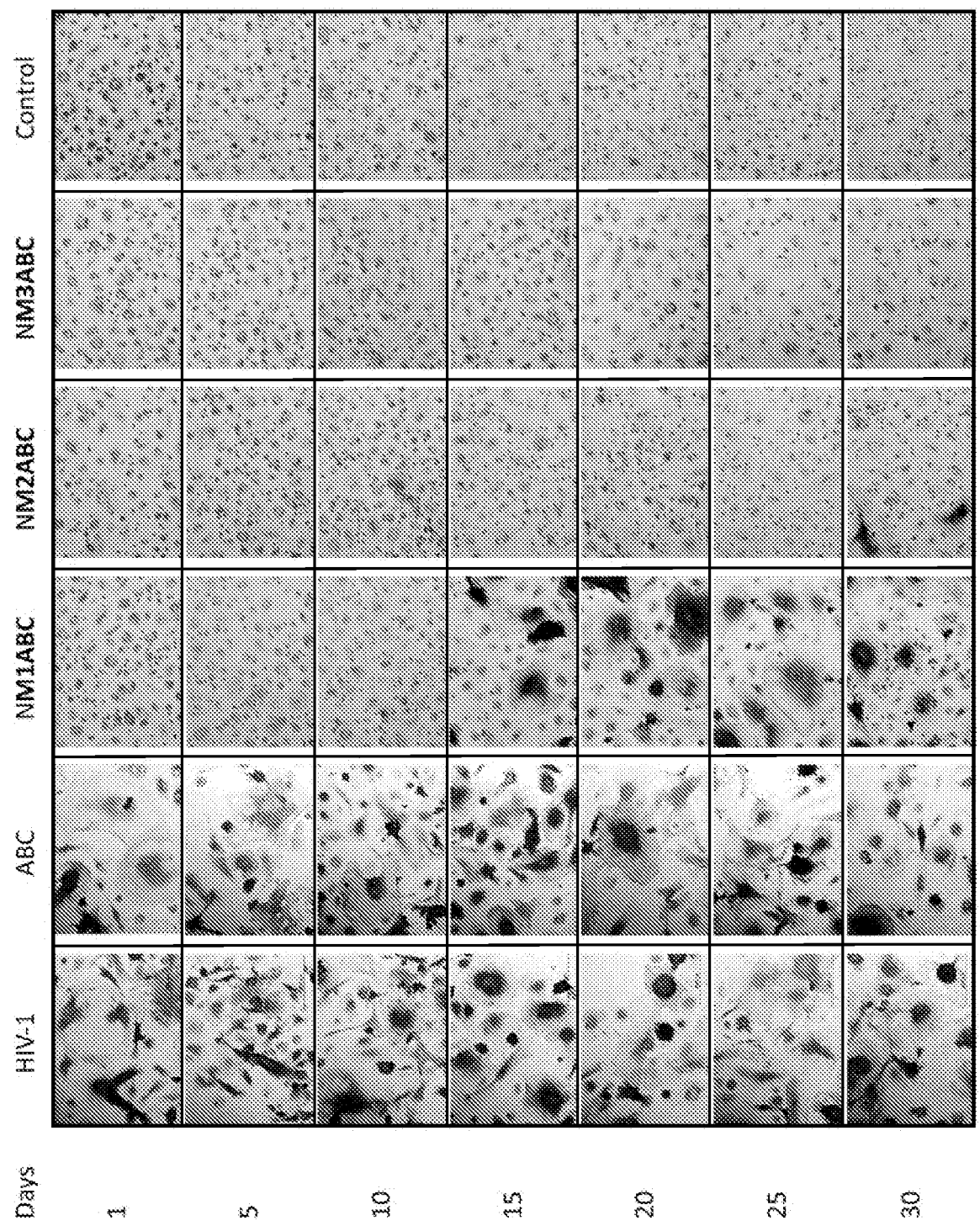
Figure 3D:
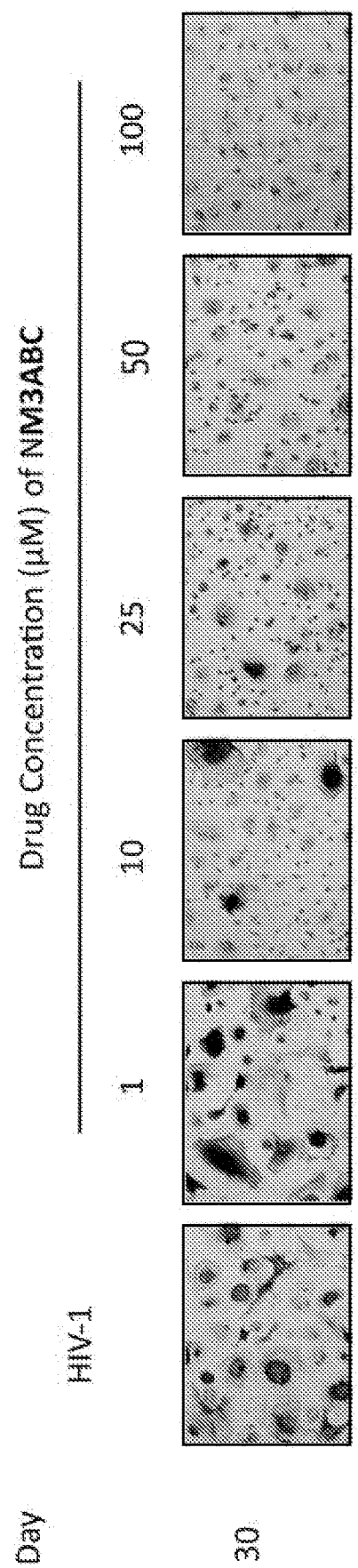

FIG. 3A provides a graph of HIV reverse transcriptase (RT) activity ten days after viral challenge in MDMs treated with nanoformulations containing 100 μM ABC equivalent for 8 hours and challenged with HIV-$1_{ADA}$ at the indicated times. RT activity was not detectable with NM2ABC or NM3ABC. FIG. 3B provides a graph of HIV RT activity in MDMs treated with NM3ABC and challenged with HIV-$1_{ADA}$. MDMs were treated with 1, 10, 25, 50 and 100 μM NM3ABC for 8 hours. At day 30 post treatment, the MDMs were challenged with HIV-$1_{ADA}$. Ten days after infection, the culture media were collected for RT assay. Data are expressed as mean±SD for n=3 samples per group. FIG. 3C provides images of MDMs stained for HIV-1 p24 antigen. MDMs treated with nanoformulations containing 100 μM ABC equivalent for 8 hours and challenged with HIV-$1_{ADA}$ at the indicated times. Ten days after infection, the cells were fixed and stained for HIV-1 p24 antigen. FIG. 3D provides images of MDMs stained for HIV-1 p24 antigen. MDMs were treated with 1, 10, 25, 50 and 100 μM NM3ABC for 8 hours. At day 30 post treatment, the MDMs were challenged with HIV-$1_{ADA}$. Ten days after infection, the cells were fixed and stained for HIV-1 p24 antigen.

Figure 4A:
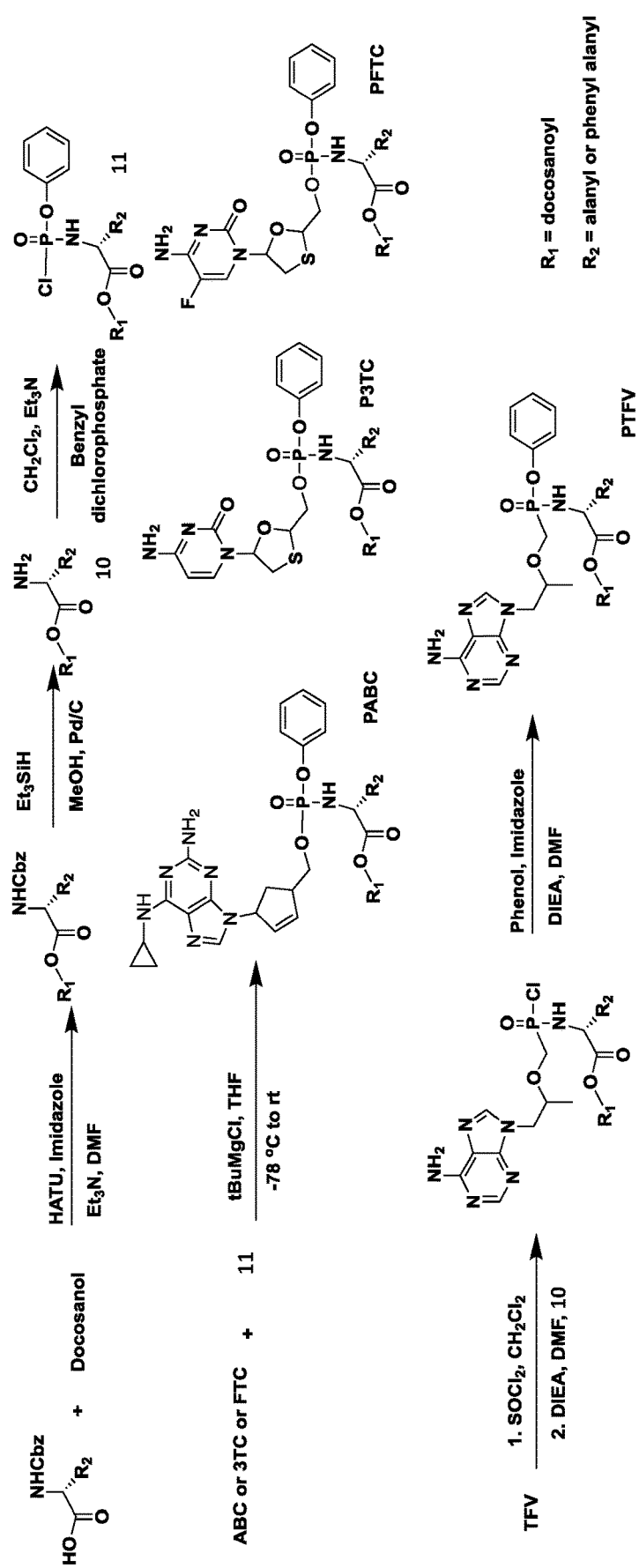
Figure 4B:
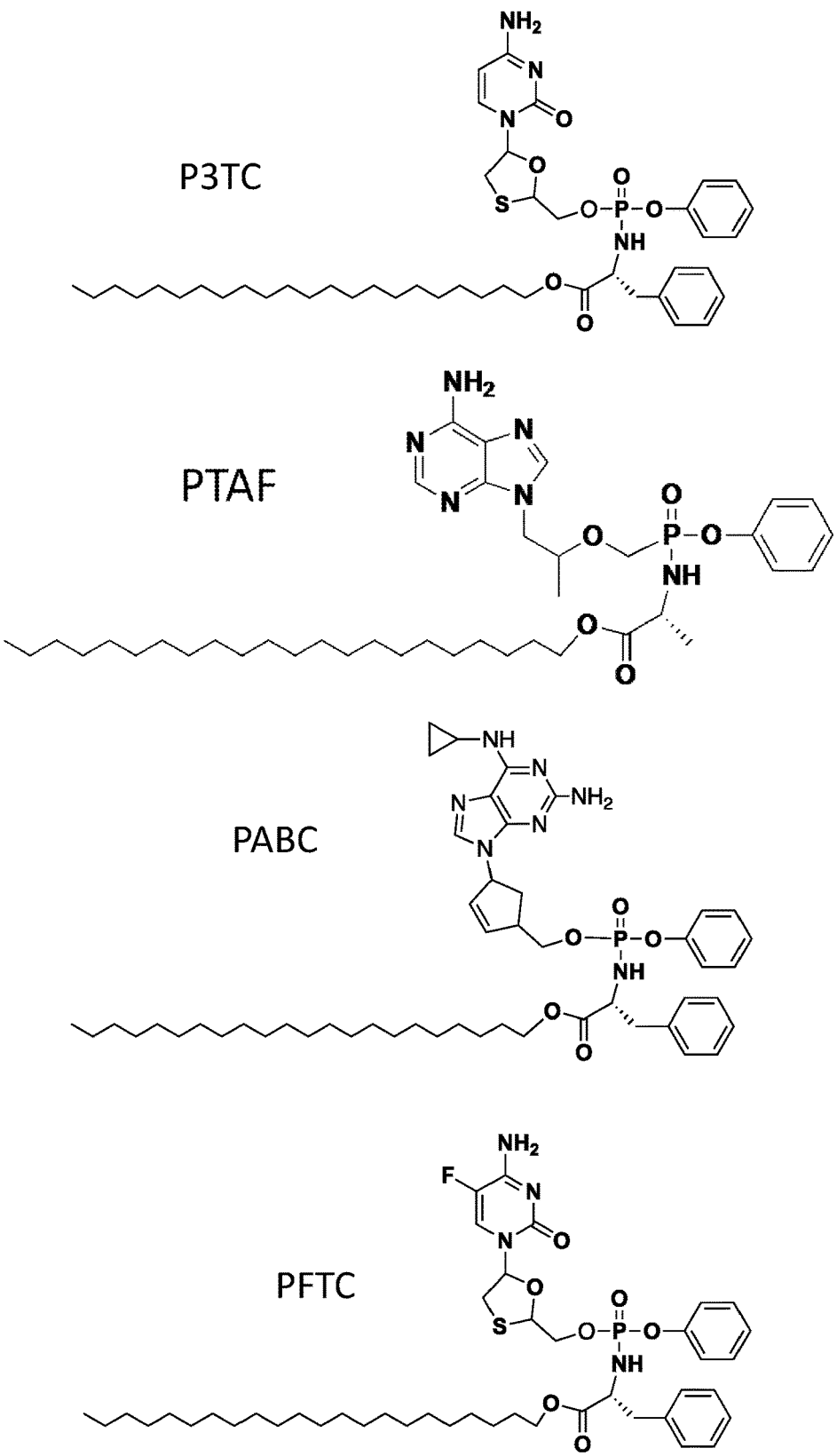

FIG. 4A provides a schematic of the synthesis of abacavir (PABC), lamivudine (P3TC), emtricitabine (PFTC) and tenofovir (PTFV) prodrugs. FIG. 4B provides structures of PABC, P3TC, PFTC, and tenofovir (tenofovir alafenamide) (PTAF) prodrugs.

Figure 5C:
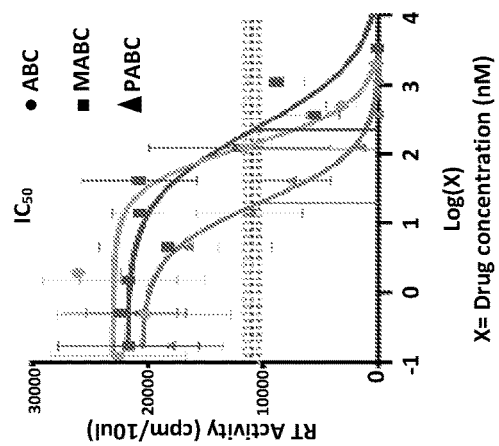
Figure 5B:
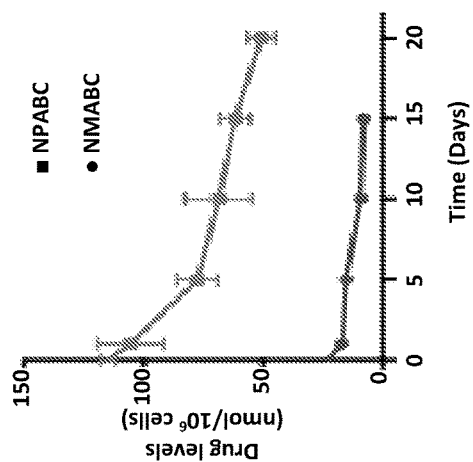
Figure 5A:
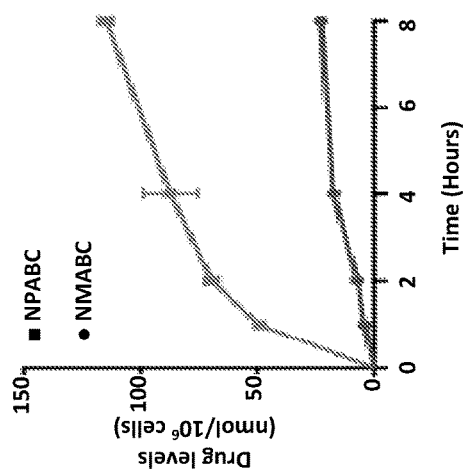

FIG. 5A provides a graph of drug uptake by MDM of equal drug concentrations (100 μM) of NPABC and NMABC. FIG. 5B provides a graph of drug retention by MDM of equal drug concentrations (100 μM) of NPABC and NMABC. FIG. 5C provides a graph of the $IC_{50}$ equal drug concentrations (100 μM) of ABC, myristoylated ABC (MABC), and PABC on reverse transcriptase. The $IC_{50}$ was 130.7, 226.7, and 20.5 nM for ABC, MABC and PABC, respectively.

Figure 6B:
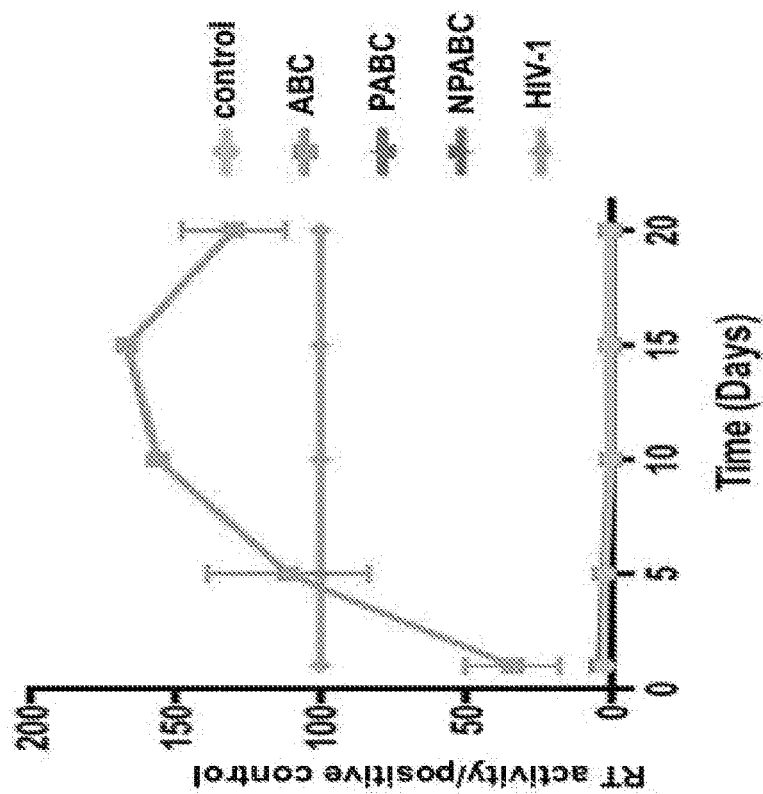
Figure 6A:
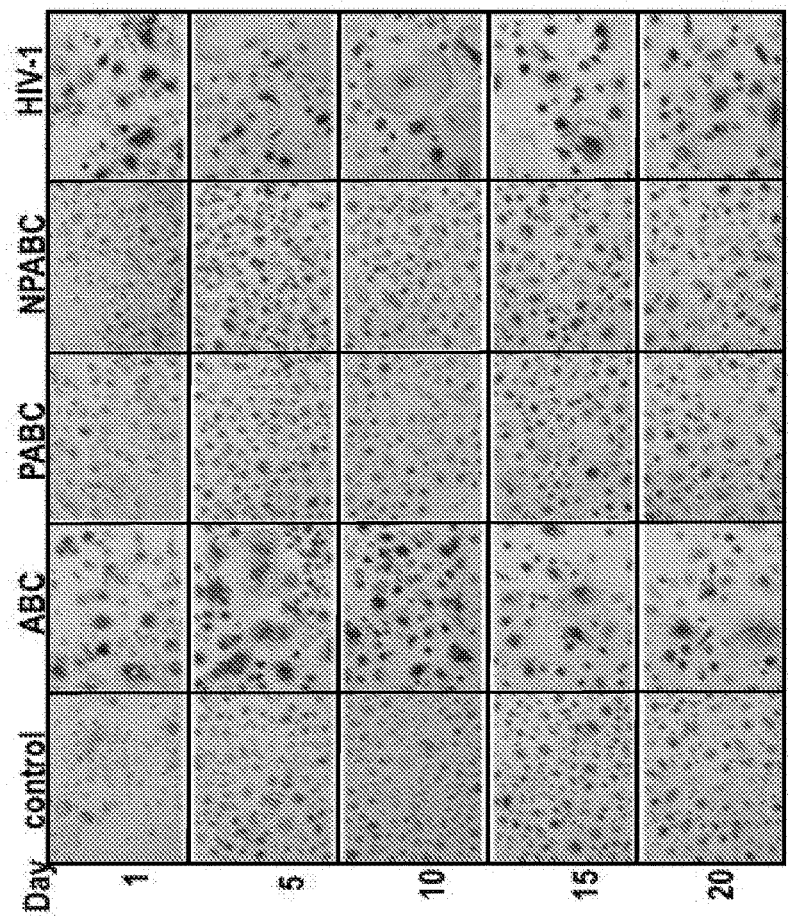

FIG. 6A provides images of HIV-1 p24 staining in virus-infected MDM pretreated with ABC, PABC, or NPABC. FIG. 6B provides a graph of HIV-1 reverse transcriptase (RT) activity in virus-infected MDM pretreated with ABC, PABC, or NPABC.

Figure 7A:
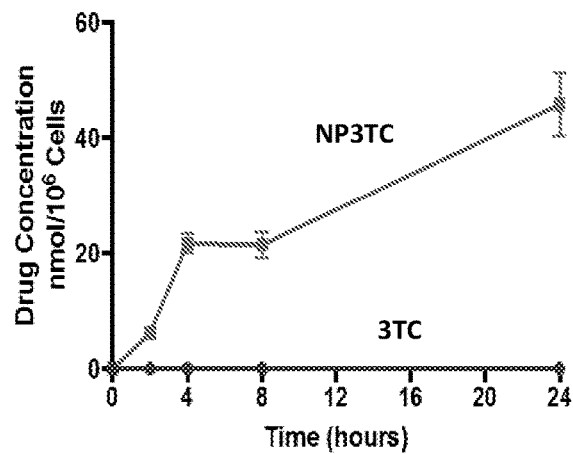
Figure 7B:
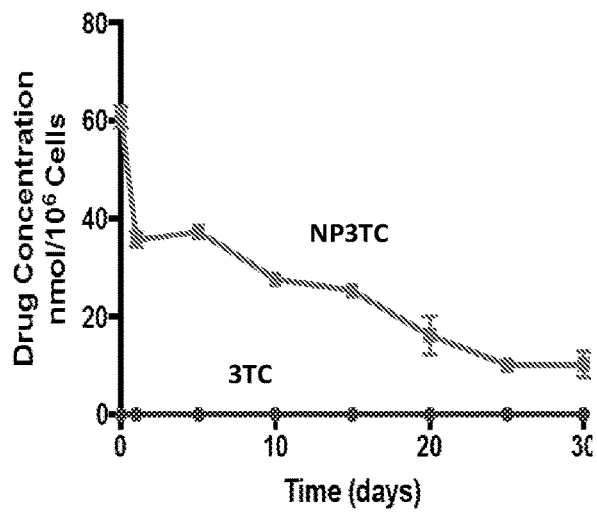
Figure 7C:
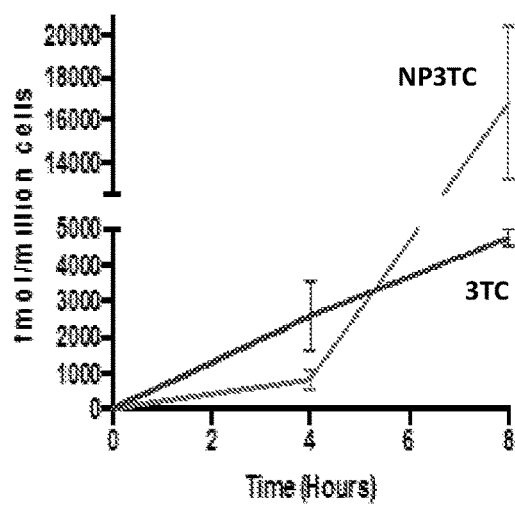
Figure 7D:
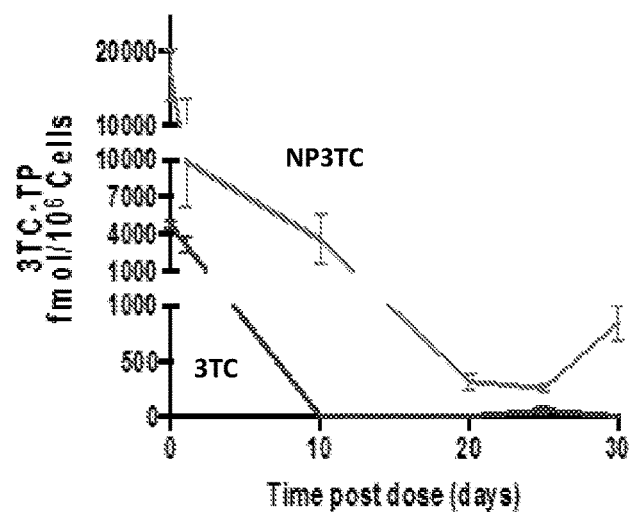

FIG. 7A provides a graph of drug uptake by MDM of equal drug concentrations (100 μM) of NP3TC and 3TC. FIG. 7B provides a graph of drug retention by MDM of equal drug concentrations (100 μM) of NP3TC and 3TC. FIG. 7C is a graph of intracellular 3TC triphosphate levels in MDM treated with NP3TC or 3TC during drug uptake. FIG. 7D is a graph of the retention of intracellular 3TC triphosphate levels in MDM treated with NP3TC or 3TC. Data are expressed as mean±SEM for n=3 samples per group.

Figure 8B:
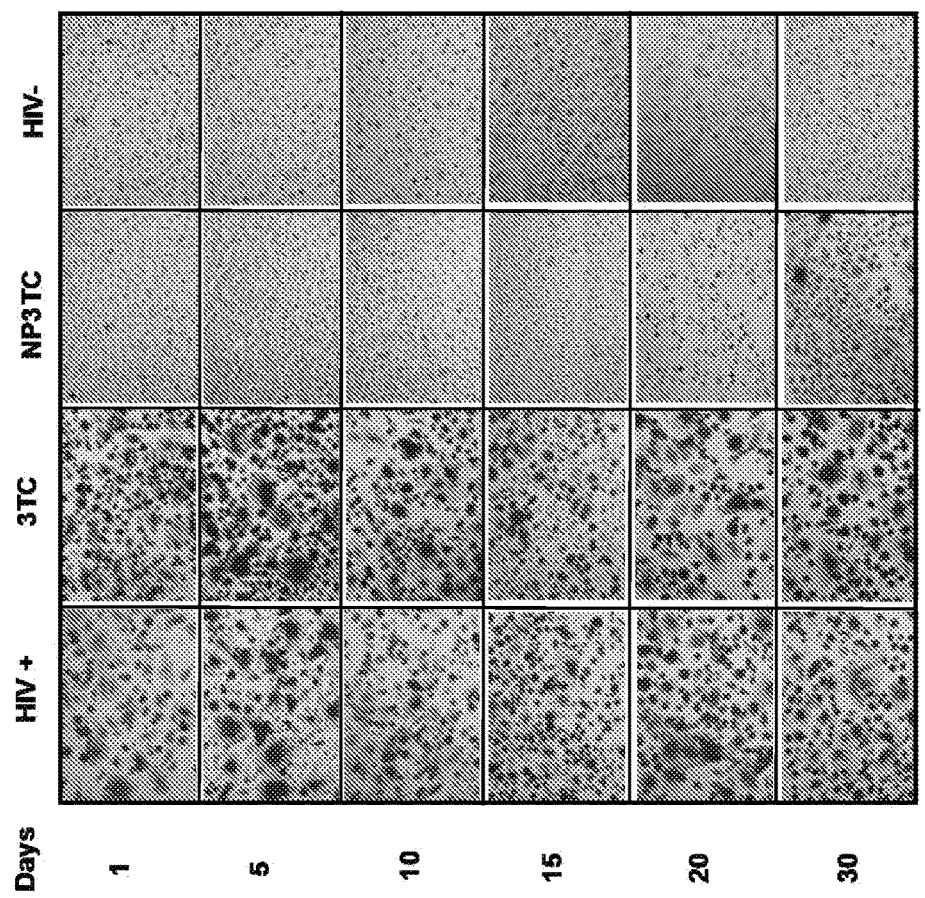
Figure 8A:
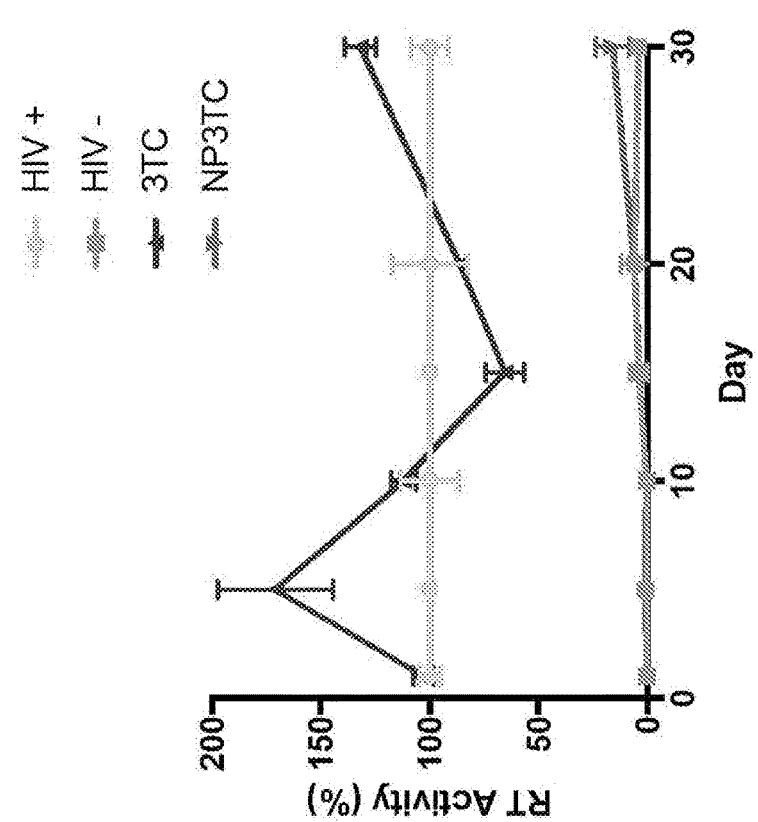

FIG. 8A provides a graph of HIV-1 reverse transcriptase (RT) activity in virus-infected MDM pretreated 3TC or NP3TC. FIG. 8B provides images of HIV-1 p24 staining in virus-infected MDM pretreated with 3TC or NP3TC.

Figure 9:
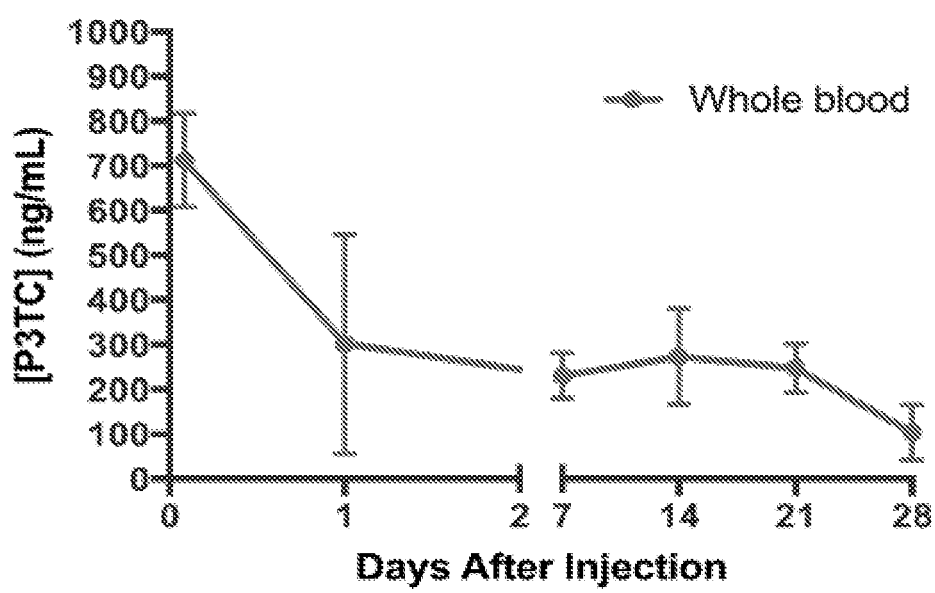

FIG. 9 provides a graph of the levels of P3TC in whole blood from Sprague Dawley rats administered a single 75 mg/kg IM dose of NP3TC. Drug concentrations were quantified by LC-MS/MS. Data are expressed as mean±SEM for n=5 rats.

Figure 10A:
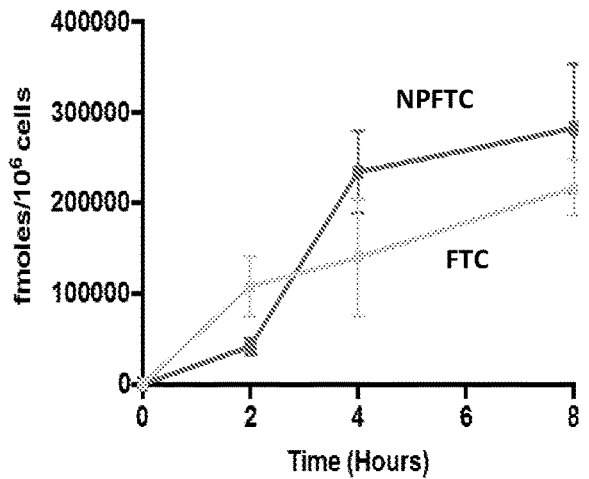
Figure 10B:
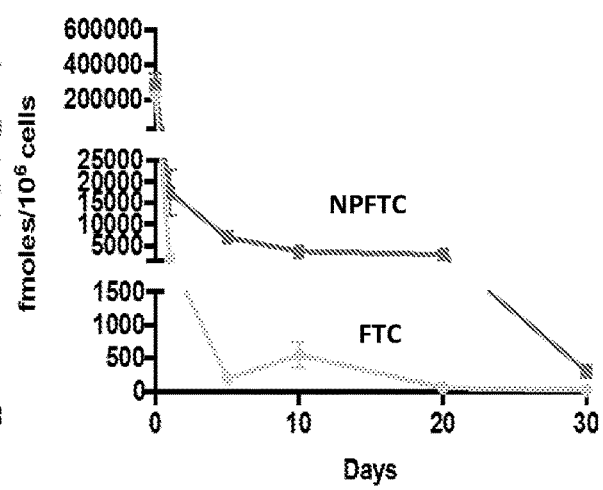
Figure 10C:
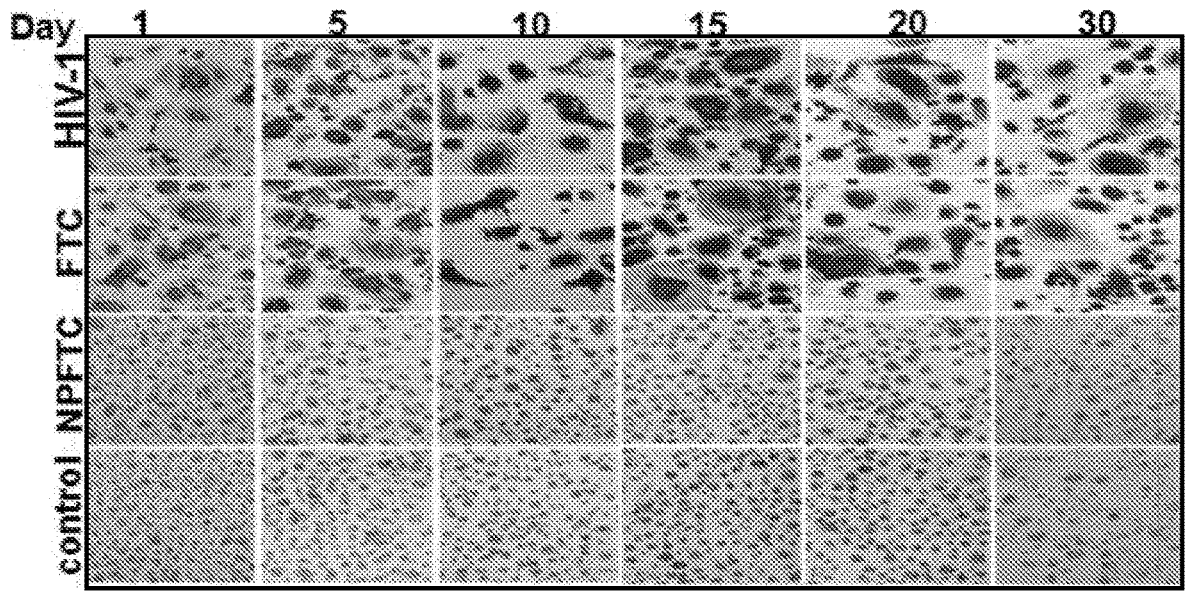

FIG. 10A is a graph of intracellular FTC triphosphate levels in MDM treated with NPFTC or FTC during drug uptake. FIG. 10B is a graph of the retention of intracellular FTC triphosphate levels in MDM treated with NPFTC or FTC. FIG. 10C provides images of HIV-1 p24 staining in virus-infected MDM pretreated with FTC or NPFTC.

Figures 11A, 11B, 11C:
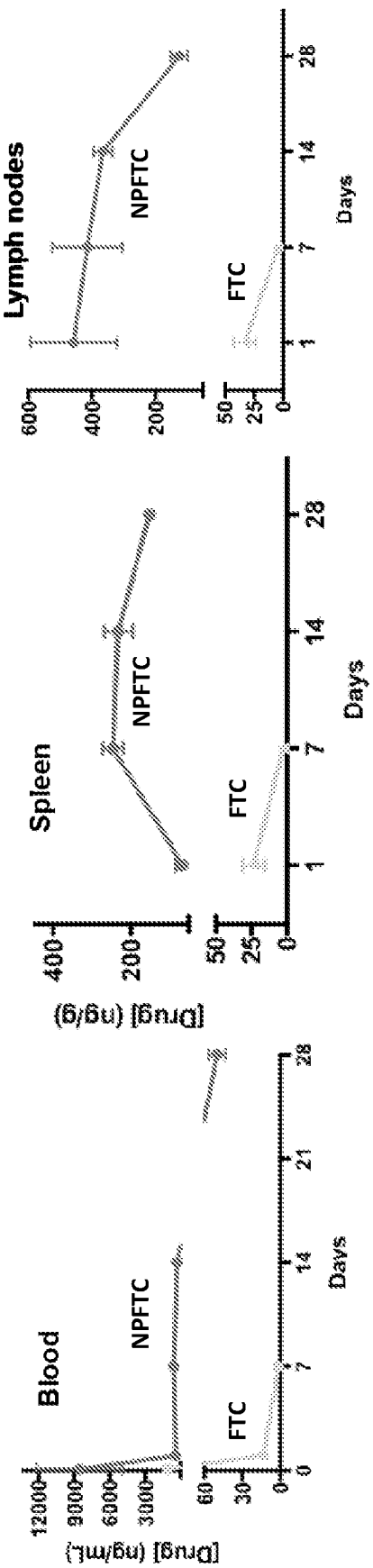

FIGS. 11A, 11B, and 11C provides a graph of the levels of PFTC in whole blood, spleen, and lymph nodes, respectively, from Sprague Dawley rats administered a single 45 mg/kg IM dose of NPFTC of FTC. Drug concentrations were quantified by LC-MS/MS. Data are expressed as mean±SEM for n=5 rats per group.

DETAILED DESCRIPTION OF THE INVENTION

Treatments of viral infections, particularly HIV infections, which are currently available, include inhibitors of viral entry, nucleoside reverse transcriptase, nucleotide reverse transcriptase, integrase, and protease. Resistance is linked to a shortened drug half-life, the viral life cycle, and rapid mutations resulting in a high genetic variability. Combination therapies, e.g., antiretroviral therapies (ART), which are considered "cocktail" therapy, have gained substantial attention. Benefits include decreased viral resistance, limited toxicities, improved adherence to therapeutic regimens and sustained antiretroviral efficacy. Combination therapies minimize potential drug resistance by suppressing viral (e.g., HIV) replication, thereby reducing spontaneous resistant mutants. Treatment failure is attributed, in part, to the short drug half-lives. Furthermore, failure can also be attributed, in part, to limited drug access to tissue and cellular viral reservoirs, thereby precluding viral eradication efforts. To these ends, the development of cell and tissue targeted nanoformulated prodrug (nanoparticle) platforms are of considerable interest in the management of viral (e.g., HIV) infections. Pre-exposure prophylaxis (PrEP) is another strategy used in the management of viral (e.g., HIV) transmission. For example, TRUVADA® (tenofovir/emtricitabine) has been approved for pre-exposure prophylaxis against HIV infection. Additionally, the combination of lamivudine and zidovudine (COMBIVIR®) has been used as pre-exposure prophylaxis and post-exposure prophylaxis.

The prodrugs and nanoformulated prodrugs (nanoparticles) provided herein extend the apparent drug half-life, increase hydrophobicity and lipophilicity, improved protein binding capacity and antiretroviral efficacy. This will benefit people who have to receive daily high doses or even several doses a day, since lower dosage with less dosing frequency would not only decrease the side effects, but also be convenient to the patients. The prodrugs and nanoformulated prodrugs (nanoparticles) provided herein may also be used as a post-exposure treatment and/or pre-exposure prophylaxis (e.g., for people who are at high risk of contracting HIV-1). In other words, the prodrugs and nanoparticles of the instant invention and their combination may be used to prevent a viral infection (e.g., HIV infection) and/or treat or inhibit an acute or long term viral infection (e.g., HIV infection). While the prodrugs and nanoparticles of the instant invention are generally described as anti-HIV agents, the prodrugs and nanoformulations of the instant invention are also effective against other viral infections including, without limitation: hepatitis B virus (HBV), hepatitis C virus (HCV), herpes simplex virus (HSV), and Ebola virus. The prodrugs and nanoformulations of the instant invention are also effective against other microbial infections such as *Mycobacterium tuberculosis*. The prodrugs and nanoformulations of the instant invention are also effective against cancer and platelet disorders.

The present invention describes novel, potent, broad spectrum prodrugs with improved biological activity over parent drugs. Methods for the encapsulation of the prodrugs into long acting slow effective formulations for efficient intracellular and tissue delivery and extended drug half-lives are also provided. The long acting slow effective release (LASER) compositions described herein exhibit enhanced potency and may be used as effective therapeutic or preventative interventions against cancer and microbial infections (e.g., viral infections).

ProTide prodrugs allow for the efficient intracellular delivery of nucleoside analogue monophosphates and monophosphonates. Typically, the hydroxyls of the monophosphate or monophosphonate groups of the ProTide prodrug are masked by an aromatic group and an amino acid ester moiety. These moieties are enzymatically cleaved-off inside cells to release the free nucleoside monophosphate and monophosphonate species. Herein, ProTides which are derivatives of nucleoside analogs conjugated to monophosphates masked with hydrophobic and lipophilic cleavable moieties (e.g., therapeutic fatty alcohols) are utilized. The hydrophobic and lipophilic cleavable moiety (e.g., therapeutic fatty alcohols) exhibit antiviral activity against enveloped viruses (Katz, et al., Ann. NY Acad. Sci. (1994) 724:472-88). Synergistic interactions between therapeutic fatty alcohols and nucleoside analogs substantially enhance antiviral potency of the nucleosides (Marcelletti, et al., Antiviral Res. (2002) 56:153-66).

As described herein, hydrophilic parent compounds are converted into lipophilic monophosphate derivatives. In a particular embodiment, the ProTide derivatizing promoieties comprise of novel labile therapeutic fatty alcohols to improve drug potency, accelerate intracellular and tissue penetrance, protein binding, and bioavailability. The hydrophobic nature of the synthesized crystalline ProTides facilitates encapsulation into long acting slow release drug nanocrystals with improved biopharmaceutical features. The nanoformulations of the instant invention (sometimes referred to as LASER PROART) may be composed of ProTide particles dispersed in sterile aqueous suspensions and stabilized by polymeric excipients, lipids, and/or surfactants or polymers. Without being bound by theory, the mechanism of drug release involves dissolution of the ProTide from the nanoparticle followed by efficient enzymatic cleavage to generate two bioactive agents, i.e., the nucleoside monophosphate analogs (e.g., to inhibit reverse transcriptase) and broad-spectrum antiviral fatty alcohols.

The benefits of the system described herein include, without limitation, improved drug potency, bioavailability and extended half-life for patient convenience. Indeed, the nanoformulations described in this invention displayed more than 100-fold increase in drug uptake by monocyte-derived macrophages (MDM) when compared to uptake of the parent drug. Also, the modified drug and nanoparticles exhibited enhanced potency through increased and extended inhibition of viral replication when compared against parent drugs. Therefore, the nanoformulations of the instant invention allow for enhancement of antiviral potency and accelerated drug delivery to anatomical reservoirs of infection.

In accordance with the instant invention, prodrugs are provided. The prodrugs may be, for example, prodrugs of a nucleoside, nucleotide, nucleobase, or analog thereof, particularly a nucleoside, nucleotide, nucleobase, or analog thereof that is a therapeutic agent. The prodrugs of the instant invention may be, for example, a phosphoramidate, ProTide, and/or ester of the nucleoside, nucleotide, nucleobase, or analog thereof In a particular embodiment, the prodrug is a nucleoside analog prodrug.

In a particular embodiment, the nucleoside analog prodrug is a ProTide derivative, particularly a ProTide derivative comprising an aliphatic or alkyl group, particularly attached to the amino acid ester moiety. In a particular embodiment, the nucleoside analog prodrug comprises a nucleoside analog conjugated to a monophosphonate or phosphoramidate group, wherein one or more of the —OH groups of the monophosphonate or phosphoramidate group is replaced with an O-aryl group and/or an amino acid (e.g., via the amino group). In a particular embodiment, the amino acid of the nucleoside analog prodrug is an amino acid ester comprising an aliphatic or alkyl group.

The nucleoside analog prodrug of the instant invention may be selected from one of Formulas (I)-(X) or a pharmaceutically acceptable salt thereof:

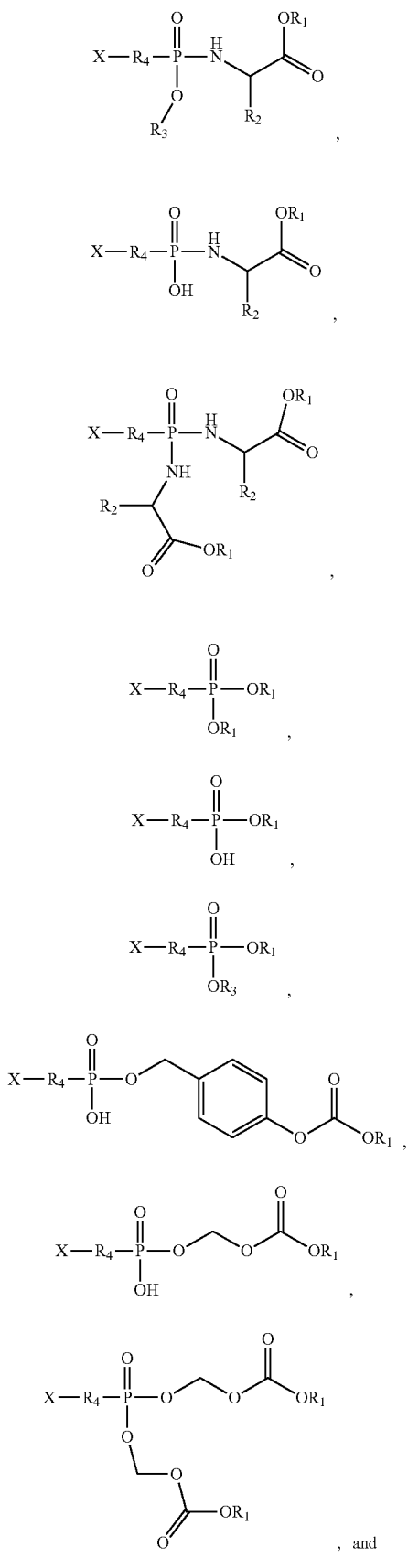

wherein:

X is a nucleoside, nucleotide, or nucleobase analog, particularly wherein the analog is a therapeutic agent. In a particular embodiment, X is a nucleoside analog. In a particular embodiment, X is a nucleoside analog reverse transcriptase inhibitor (NRTI).

$R_1$ is an aliphatic or alkyl group. The aliphatic or alkyl group may be unsaturated or saturated, and may be substituted with at least one heteroatom (e.g., O, N, or S). In a particular embodiment, the alkyl or aliphatic group is hydrophobic. In a particular embodiment, the alkyl or aliphatic group comprises about 3 to about 30 carbons (e.g., in the main chain of the alkyl or aliphatic group). In a particular embodiment, $R_1$ is a C4-C24 unsaturated or saturated alkyl or aliphatic group, which may be substituted with at least one heteroatom (e.g., O, N, or S). In a particular embodiment, $R_1$ is a C13-C24 unsaturated or saturated alkyl or aliphatic group, which may be substituted with at least one heteroatom (e.g., O, N, or S). In a particular embodiment, $R_1$ is a C18-C24 unsaturated or saturated alkyl or aliphatic group, which may be substituted with at least one heteroatom (e.g., O, N, or S). In a particular embodiment, $R_1$ is the alkyl chain of a fatty acid (saturated or unsaturated), particularly a C13-C24 fatty acid or a C18-C24 fatty acid. In a particular embodiment, $R_1$ is behenoyl or docosyl.

$R_2$ is hydrogen, alkyl group, or aryl group. The alkyl or aryl group may be substituted. The alkyl group may be unsaturated or saturated and may be substituted with at least one heteroatom (e.g., O, N, or S). The aryl group may be substituted with an alkyl group and/or may be substituted with at least one heteroatom (e.g., O, N, or S). In a particular embodiment, $R_2$ is any D or L amino acid side chain. In a particular embodiment, $R_2$ is the side chain of phenylalanine, alanine, leucine, or to tyrosine. In a particular embodiment, $R_2$ is selected from the group consisting of H, phenyl, $CH_3$, —$CH_2iPr$, —$CH_2Ph$, and —$CH_2PhOH$.

$R_3$ is an optionally substituted aryl group. The aryl group may be substituted with a halide (e.g., F, Cl, or Br) and/or may be substituted with at least one heteroatom (e.g., O, N, or S). In a particular embodiment, $R_3$ is phenyl or naphthyl (e.g., 1-naphthol).

$R_4$ is an alkyl group, substituted carbon atom, or a heteroatom (e.g., O, N, or S). The alkyl group may be unsaturated or saturated, and may be substituted with at least one heteroatom (e.g., O, N, or S). In a particular embodiment, the alkyl group comprises about 1 to about 3 carbons (e.g., in the main chain of the alkyl or aliphatic group). In a particular embodiment, the alkyl group is $CH_2$.

In a particular embodiment, the nucleoside analog prodrug of the instant invention is selected from:
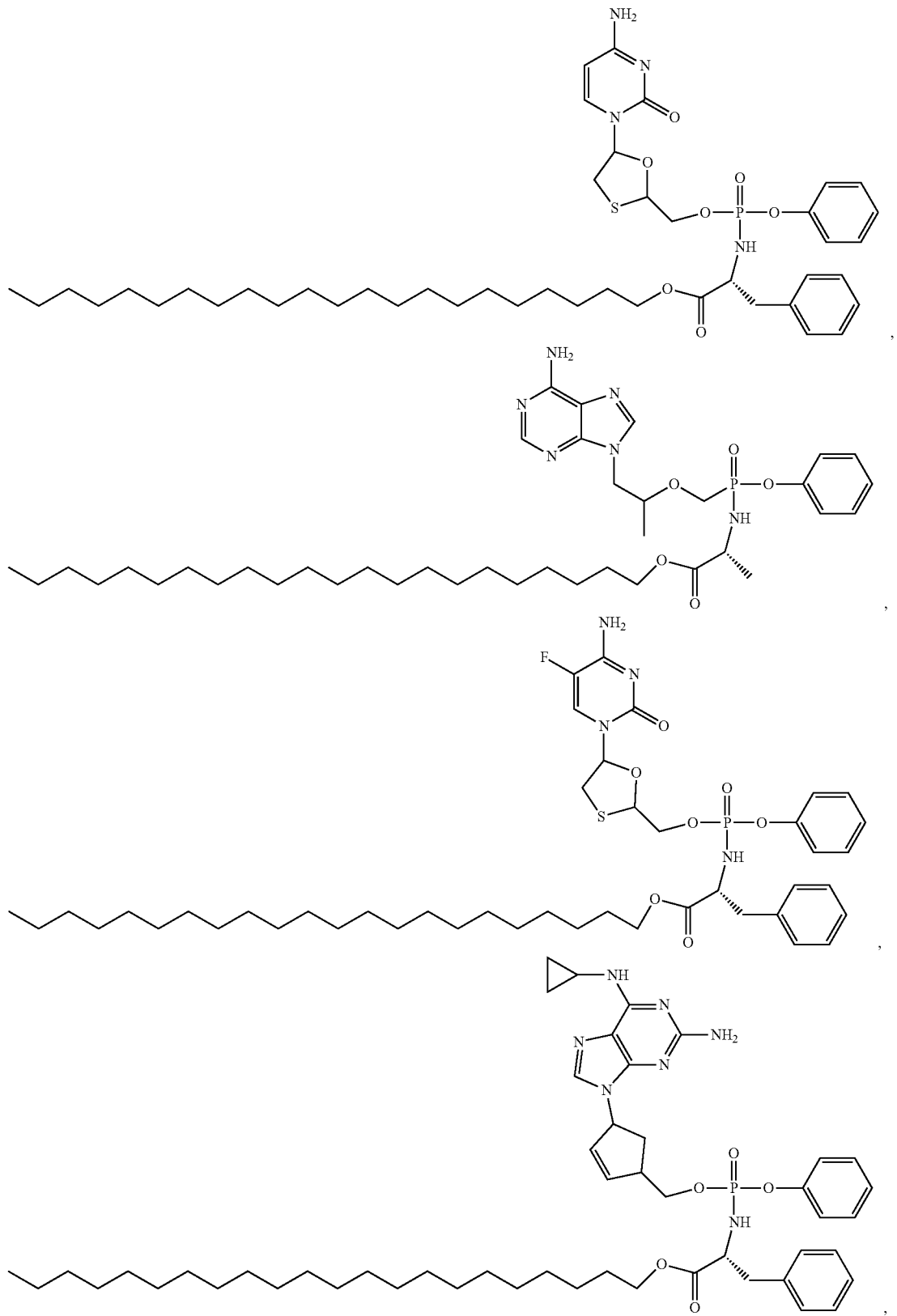
and pharmaceutically acceptable salts thereof.

As stated hereinabove, X may be any nucleoside, nucleotide, nucleobase, or analog thereof. In a particular embodiment, X is a known therapeutic agent or drug. In a particular embodiment, the prodrug is a prodrug of a nucleoside analog reverse transcriptase inhibitor (NRTI). Examples of nucleosides, nucleotides, nucleobases, and analogs thereof include, without limitation, abacavir (ABC), lamivudine (3TC), emtricitabine (FTC), tenofovir (TFV), tenofovir alafenamide (TAF), tenofovir disoproxil fumarate, didanosine, vidarabine, BCX4430, cytarabine, gemcitabine, zalcitabine, entecavir, acyclovir, valacyclovir, ganciclovir, valganciclovir, penciclovir, famciclovir, brivudine, cidofovir, sofosbuvir, adefovir, adefovir dipivoxil, laninamivir, stavudine, telbivudine, zidovudine, ribavirin, idoxuridine, trifluridine, ticagrelor, cangrelor, 5-fluorouracil (5-FU), 5-bromo-2-deoxy-uridine, capecitabine, cladribine, capecitabine, 4'-ethynyl-2-fluoro-2'-deoxyadenosine (EFdA), and fludarabine. Examples of nucleoside-analog reverse transcriptase inhibitors include, without limitation, abacavir (ABC), lamivudine (3TC), emtricitabine (FTC), tenofovir (TFV), telbivudine, entecavir, zidovudine, adefovir dipivoxil, adefovir, stavudine, didanosine, emtricitabine, and zalcitabine. In a particular embodiment, the nucleoside-analog reverse transcriptase inhibitor is selected from the group consisting of abacavir (ABC), lamivudine (3TC), emtricitabine (FTC), tenofovir (TFV), telbivudine, entecavir, and zidovudine. In a particular embodiment, the nucleoside analog is selected from the group consisting of abacavir (ABC), lamivudine (3TC), emtricitabine (FTC), and tenofovir (TFV).

The instant invention also encompasses nanoparticles (sometimes referred to herein as nanoformulations) comprising the prodrug of the instant invention. The nanoparticles may be used for the delivery of the compounds to a cell or host (e.g., in vitro or in vivo). In a particular embodiment, the nanoparticle is used for the delivery of antiretroviral therapy to a subject. The nanoparticles of the instant invention comprise at least one prodrug and at least one surfactant or polymer. In a particular embodiment, the nanoparticles comprise a spectroscopic-defined surfactant/polymer:drug ratio that maintains optimal targeting of the drug nanoparticle to maintain a macrophage depot. These components of the nanoparticle, along with other optional components, are described hereinbelow.

Methods of synthesizing the nanoparticles of the instant invention are known in the art. In a particular embodiment, the methods generate nanoparticles comprising a prodrug (e.g., crystalline or amorphous) coated (either partially or completely) with a polymer and/or surfactant. Examples of synthesis methods include, without limitation, milling (e.g., wet milling), homogenization (e.g., high pressure homogenization), particle replication in nonwetting template (PRINT) technology, and/or sonication techniques. For example, U.S. Patent Application Publication No. 2013/0236553, incorporated by reference herein, provides methods suitable for synthesizing nanoparticles of the instant invention. In a particular embodiment, the polymers or surfactants are firstly chemically modified with targeting ligands and then used directly or mixed with non-targeted polymers or surfactants in certain molar ratios to coat on the surface of prodrug suspensions—e.g., by using a nanoparticle synthesis process (e.g., a crystalline nanoparticle synthesis process) such as milling (e.g., wet milling), homogenization (e.g., high pressure homogenization), particle replication in nonwetting template (PRINT) technology, and/or sonication techniques, thereby preparing targeted nanoformulations. The nanoparticles may be used with or without further purification, although the avoidance of further purification is desirable for quicker production of the nanoparticles. In a particular embodiment, the nanoparticles are synthesized using milling and/or homogenization. Targeted nanoparticles (e.g., using ligands with high molecular weight) may be developed through either physically or chemically coating and/or binding on the surface of polymers or surfactants and/or drug nanosuspensions.

In a particular embodiment, the nanoparticles of the instant invention are synthesized by adding the prodrug (e.g., crystals) to a polymer or surfactant solution and then generating the nanoparticles (e.g., by wet milling or high pressure homogenization). The prodrug and polymer or surfactant solution may be agitated prior the wet milling or high pressure homogenization.

The nanoparticles of the instant invention may be used to deliver at least one prodrug of the instant invention to a cell or a subject (including non-human animals). The nanoparticles of the instant invention may further comprise at least one other agent or compound, particularly a bioactive agent, particularly a therapeutic agent (e.g., antiviral compound) or diagnostic agent, particularly at least one antiviral or antiretroviral. In a particular embodiment, the nanoparticles of the instant invention comprise at least two therapeutic agents, particularly wherein at least one is a prodrug of the instant invention. For example, the nanoparticle may comprise a nucleoside-analog reverse transcriptase inhibitor (NRTI) prodrug of the instant invention and at least one other therapeutic agent (e.g., an anti-HIV agent). The nanoparticle may comprise a 3TC, ABC, FTC, and/or TFV prodrug of the instant invention and at least one other therapeutic agent (e.g., an anti-HIV agent).

In a particular embodiment, the nanoparticles of the instant invention are a submicron colloidal dispersion of nanosized prodrug crystals stabilized by polymers or surfactants (e.g., surfactant-coated drug crystals; a nanoformulation). In a particular embodiment, the prodrug may be crystalline (solids having the characteristics of crystals), amorphous, or are solid-state nanoparticles of the prodrug that is formed as crystal that combines the drug and polymer or surfactant. In a particular embodiment, the prodrug is crystalline. As used herein, the term "crystalline" refers to an ordered state (i.e., non-amorphous) and/or a substance exhibiting long-range order in three dimensions. In a particular embodiment, the majority (e.g., at least 50%, 60%, 70%, 80%, 90%, 95% or more) of the prodrug and, optionally, the hydrophobic portion of the surfactant are crystalline.

In a particular embodiment, the nanoparticle of the instant invention is up to about 2 or 3 µm in diameter (e.g., z-average diameter) or its longest dimension, particularly up to about 1 µm (e.g., about 100 nm to about 1 µm). For example, the diameter or longest dimension of the nanoparticle may be about 50 to about 800 nm. In a particular embodiment, the diameter or longest dimension of the nanoparticle is about 50 to about 750 nm, about 50 to about 500 nm, about 200 nm to about 500 nm, or about 200 nm to about 400 nm. The nanoparticles may be, for example, rod shaped, elongated rods, irregular, or round shaped. The nanoparticles of the instant invention may be neutral or charged. The nanoparticles may be charged positively or negatively.

As stated hereinabove, the nanoparticles of the instant invention comprise at least one polymer or surfactant. A "surfactant" refers to a surface-active agent, including substances commonly referred to as wetting agents, detergents, dispersing agents, or emulsifying agents. Surfactants are usually organic compounds that are amphiphilic.

Examples of polymers or surfactants include, without limitation, synthetic or natural phospholipids, PEGylated lipids (e.g., PEGylated phospholipid), lipid derivatives, polysorbates, amphiphilic copolymers, amphiphilic block copolymers, poly(ethylene glycol)-co-poly(lactide-co-glycolide) (PEG-PLGA), their derivatives, ligand-conjugated derivatives and combinations thereof. Other polymers or surfactants and their combinations that can form stable nanosuspensions and/or can chemically/physically bind to the targeting ligands of HIV infectable/infected CD4+ T cells, macrophages and dendritic cells can be used in the instant invention. Further examples of polymers or surfactants include, without limitation: 1) nonionic surfactants (e.g., pegylated and/or polysaccharide-conjugated polyesters and other hydrophobic polymeric blocks such as poly(lactide-co-glycolide) (PLGA), polylactic acid (PLA), polycaprolactone (PCL), other polyesters, poly(propylene oxide), poly(1,2-butylene oxide), poly(n-butylene oxide), poly(tetrahydrofurane), and poly(styrene); glyceryl esters, polyoxyethylene fatty alcohol ethers, polyoxyethylene sorbitan fatty acid esters, polyoxyethylene fatty acid esters, sorbitan esters, glycerol monostearate, polyethylene glycols, polypropyleneglycols, cetyl alcohol, cetostearyl alcohol, stearyl alcohol, aryl alkyl polyether alcohols, polyoxyethylene-polyoxypropylene copolymers, poloxamines, cellulose, methylcellulose, hydroxylmethylcellulose, hydroxypropylcellulose, hydroxypropylmethylcellulose, polysaccharides, starch and their derivatives, hydroxyethylstarch, polyvinyl alcohol (PVA), polyvinylpyrrolidone, and their combination thereof); and 2) ionic surfactants (e.g., phospholipids, amphiphilic lipids, 1,2-dialkylglycero-3-alkylphophocholines, 1, 2-distearoyl-sn-glecro-3-phosphocholine (DSPC), 1,2-distearoyl-sn-glycero-3-phosphoethanolamine-N-[carboxy(polyethylene glycol) (DSPE-PEG), dimethylaminoethanecarbamoyl cheolesterol (DC-Chol), N-[1-(2,3-Dioleoyloxy)propyl]-N,N,N-trimethylammonium (DOTAP), alkyl pyridinium halides, quaternary ammonium compounds, lauryldimethylbenzylammonium, acyl carnitine hydrochlorides, dimethyldioctadecylammonium (DDAB), n-octylamines, oleylamines, benzalkonium, cetyltrimethylammonium, chitosan, chitosan salts, poly(ethylenimine) (PEI), poly(N-isopropyl acrylamide (PNIPAM), and poly (allylamine) (PAH), poly (dimethyldiallylammonium chloride) (PDDA), alkyl sulfonates, alkyl phosphates, alkyl phosphonates, potassium laurate, triethanolamine stearate, sodium lauryl sulfate, sodium dodecylsulfate, alkyl polyoxyethylene sulfates, alginic acid, alginic acid salts, hyaluronic acid, hyaluronic acid salts, gelatins, dioctyl sodium sulfosuccinate, sodium carboxymethylcellulose, cellulose sulfate, dextran sulfate and carboxymethylcellulose, chondroitin sulfate, heparin, synthetic poly(acrylic acid) (PAA), poly (methacrylic acid) (PMA), poly(vinyl sulfate) (PVS), poly(styrene sulfonate) (PSS), bile acids and their salts, cholic acid, deoxycholic acid, glycocholic acid, taurocholic acid, glycodeoxycholic acid, derivatives thereof, and combinations thereof).

The polymer or surfactant of the instant invention may be charged or neutral. In a particular embodiment, the polymer or surfactant is neutral or negatively charged (e.g., poloxamers, polysorbates, phospholipids, and their derivatives).

In a particular embodiment, the polymer or surfactant is an amphiphilic block copolymer or lipid derivative. In a particular embodiment, at least one polymer or surfactant of the nanoparticle is an amphiphilic block copolymer, particularly a copolymer comprising at least one block of poly (oxyethylene) and at least one block of poly(oxypropylene). In a particular embodiment, the polymer or surfactant is a triblock amphiphilic block copolymer. In a particular embodiment, the polymer or surfactant is a triblock amphiphilic block copolymer comprising a central hydrophobic block of polypropylene glycol flanked by two hydrophilic blocks of polyethylene glycol. In a particular embodiment, the surfactant is poloxamer 407.

In a particular embodiment, the amphiphilic block copolymer is a copolymer comprising at least one block of poly(oxyethylene) and at least one block of poly(oxypropylene). In a particular embodiment, the amphiphilic block copolymer is a poloxamer. Examples of poloxamers include, without limitation, Pluronic® L31, L35, F38, L42, L43, L44, L61, L62, L63, L64, P65, F68, L72, P75, F77, L81, P84, P85, F87, F88, L92, F98, L101, P103, P104, P105, F108, L121, L122, L123, F127, 10R5, 10R8, 12R3, 17R1, 17R2, 17R4, 17R8, 22R4, 25R1, 25R2, 25R4, 25R5, 25R8, 31R1, 31R2, and 31R4. In a particular embodiment, the poloxamer is poloxamer 407 (Pluronic® F127).

In a particular embodiment of the invention, the polymer or surfactant is present in the nanoparticle and/or solution to synthesize the nanoparticle (as described herein) at a concentration ranging from about 0.0001% to about 10% or 15% by weight. In a particular embodiment, the concentration of the polymer or surfactant ranges from about 0.01% to about 15%, about 0.01% to about 10%, or about 0.1% to about 6% by weight. In a particular embodiment, the nanoparticle comprises at least about 50%, 75%, 80%, 85%, 90%, 95%, 97%, 98%, 99% or higher therapeutic agent (prodrug) by weight. In a particular embodiment, the nanoparticles comprise a defined drug:polymer/surfactant ratio. In a particular embodiment, the drug:polymer/surfactant ratio (e.g., by weight) is from about 10:6 to about 1000:6, about 20:6 to about 500:6, about 50:6 to about 200:6, or about 100:6.

As stated hereinabove, the polymer or surfactant of the instant invention may be linked to a targeting ligand. The targeting of the nanoparticles (e.g., to macrophage) can provide for superior targeting, decreased excretion rates, decreased toxicity, and prolonged half-life compared to free drug or non-targeted nanoparticles. A targeting ligand is a compound that specifically binds to a specific type of tissue or cell type (e.g., in a desired target:cell ratio). For example, a targeting ligand may be used for engagement or binding of a target cell (e.g., a macrophage) surface marker or receptor which may facilitate its uptake into the cell (e.g., within a protected subcellular organelle that is free from metabolic degradation). In a particular embodiment, the targeting ligand is a ligand for a cell surface marker/receptor. The targeting ligand may be an antibody or fragment thereof immunologically specific for a cell surface marker (e.g., protein or carbohydrate) preferentially or exclusively expressed on the targeted tissue or cell type. The targeting ligand may be linked directly to the polymer or surfactant or via a linker. Generally, the linker is a chemical moiety comprising a covalent bond or a chain of atoms that covalently attaches the ligand to the polymer or surfactant. The linker can be linked to any synthetically feasible position of the ligand and the polymer or surfactant. Exemplary linkers may comprise at least one optionally substituted; saturated or unsaturated; linear, branched or cyclic aliphatic group, an alkyl group, or an optionally substituted aryl group. The linker may be a lower alkyl or aliphatic. The linker may also be a polypeptide (e.g., from about 1 to about 10 amino acids, particularly about 1 to about 5). In a particular embodiment, the targeting moiety is linked to either or both ends of the polymer or surfactant. The linker may be non-degradable and may be a covalent bond or any other chemical structure which cannot be substantially cleaved or cleaved at all under physiological environments or conditions.

The nanoparticles/nanoformulations of the instant invention may comprise targeted and/or non-targeted polymers or surfactants. In a particular embodiment, the molar ratio of targeted and non-targeted polymers or surfactants in the nanoparticles/nanoformulations of the instant invention is from about 0.001 to 100%, about 1% to about 99%, about 5% to about 95%, about 10% to about 90%, about 25% to about 75%, about 30% to about 60%, or about 40%. In a particular embodiment, the nanoparticle comprises only targeted polymers or surfactants. In a particular embodiment, the nanoparticles/nanoformulations of the instant invention comprise a folate targeted polymer or surfactant and a non-targeted version of the polymer or surfactant. In a particular embodiment, the nanoparticles/nanoformulations of the instant invention comprise folate-poloxamer 407 (FA-P407) and/or poloxamer 407.

Examples of targeting ligands include but are not limited to macrophage targeting ligands, CD4+ T cell targeting ligands, dendritic cell targeting ligands, and tumor targeting ligands. In a particular embodiment, the targeting ligand is a macrophage targeting ligand. The targeted nanoformulations of the instant invention may comprise a targeting ligand for directing the nanoparticles to HIV tissue and cellular sanctuaries/reservoirs (e.g., central nervous system, gut associated lymphoid tissues (GALT), CD4+ T cells, macrophages, dendritic cells, etc.). Macrophage targeting ligands include, without limitation, folate receptor ligands (e.g., folate (folic acid) and folate receptor antibodies and fragments thereof (see, e.g., Sudimack et al. (2000) Adv. Drug Del. Rev., 41:147-162)), mannose receptor ligands (e.g., mannose), formyl peptide receptor (FPR) ligands (e.g., N-formyl-Met-Leu-Phe (fMLF)), and tuftsin (the tetrapeptide Thr-Lys-Pro-Arg). Other targeting ligands include, without limitation, hyaluronic acid, gp120 and peptide fragments thereof, and ligands or antibodies specific for CD4, CCR5, CXCR4, CD7, CD111, CD204, CD49a, CD29, CD19, CD20, CD22, CD171, CD33, Leis-Y, WT-1, ROR1, MUC16, MUC1, MUC4, estrogen receptor, transferrin receptors, EGF receptors (e.g. HER2), folate receptor, VEGF receptor, FGF receptor, androgen receptor, NGR, Integrins, and GD2. In a particular embodiment, the targeting ligand is folic acid.

As stated hereinabove, the nanoparticles of the instant invention may comprise a further therapeutic agent. The instant invention also encompasses therapeutic methods wherein the prodrug and/or nanoparticles of the instant invention are co-administered with another therapeutic agent. In a particular embodiment, the therapeutic agent is hydrophobic, a water insoluble compound, or a poorly water soluble compound, particularly when included in the nanoparticle. For example, the therapeutic agent may have a solubility of less than about 10 mg/ml, less than 1 mg/ml, more particularly less than about 100 µg/ml, and more particularly less than about 25 µg/ml in water or aqueous media in a pH range of 0-14, preferably between pH 4 and 10, particularly at 20° C.

In a particular embodiment, the therapeutic agent is an antiviral or an antiretroviral. The antiretroviral may be effective against or specific to lentiviruses. Lentiviruses include, without limitation, human immunodeficiency virus (HIV) (e.g., HIV-1, HIV-2), bovine immunodeficiency virus (BIV), feline immunodeficiency virus (FIV), simian immunodeficiency virus (SIV), and equine infectious anemia virus (EIA). In a particular embodiment, the therapeutic agent is an anti-HIV agent. An anti-HIV compound or an anti-HIV agent is a compound which inhibits HIV (e.g., inhibits HIV replication and/or infection). Examples of anti-HIV agents include, without limitation:

(I) Nucleoside-analog reverse transcriptase inhibitors (NRTIs). NRTIs refer to nucleosides and nucleotides and analogues thereof that inhibit the activity of reverse transcriptase, particularly HIV-1 reverse transcriptase. NRTIs comprise a sugar and base. Examples of nucleoside-analog reverse transcriptase inhibitors include, without limitation, adefovir dipivoxil, adefovir, lamivudine, telbivudine, entecavir, tenofovir, stavudine, abacavir, didanosine, emtricitabine, zalcitabine, and zidovudine.

(II) Non-nucleoside reverse transcriptase inhibitors (NNRTIs). NNRTIs are allosteric inhibitors which bind reversibly at a nonsubstrate-binding site on reverse transcriptase, particularly the HIV reverse transcriptase, thereby altering the shape of the active site or blocking polymerase activity. Examples of NNRTIs include, without limitation, delavirdine (BHAP, U-90152; RESCRIPTOR®), efavirenz (DMP-266, SUSTIVA®), nevirapine (VIRAMUNE®), PNU-142721, capravirine (S-1153, AG-1549), emivirine (+)-calanolide A (NSC-675451) and B, etravirine (TMC-125), rilpivirne (TMC278, EdurantTM), DAPY (TMC120), BILR-355 BS, PHI-236, and PHI-443 (TMC-278).

(III) Protease inhibitors (PI). Protease inhibitors are inhibitors of a viral protease, particularly the HIV-1 protease. Examples of protease inhibitors include, without limitation, darunavir, amprenavir (141W94, AGENERASE®), tipranivir (PNU-140690, APTIVUS®), indinavir (MK-639; CRIXIVAN®), saquinavir (INVIRASE®, FORTOVASE®), fosamprenavir (LEXIVA®), lopinavir (ABT-378), ritonavir (ABT-538, NORVIR®), atazanavir (REYATAZ®), nelfinavir (AG-1343, VIRACEPT®), lasinavir (BMS-234475/CGP-61755), BMS-2322623, GW-640385X (VX-385), AG-001859, and SM-309515.

(IV) Fusion or entry inhibitors. Fusion or entry inhibitors are compounds, such as peptides, which block HIV entry into a cell (e.g., by binding to HIV envelope protein and blocking the structural changes necessary for the virus to fuse with the host cell). Examples of fusion inhibitors include, without limitation, CCR5 receptor antagonists (e.g., maraviroc (Selzentry®, Celsentri)), enfuvirtide (INN, FUZEON®), T-20 (DP-178, FUZEON®) and T-1249.

(V) Integrase inhibitors. Integrase inhibitors are a class of antiretroviral drug designed to block the action of integrase (e.g., HIV integrase), a viral enzyme that inserts the viral genome into the DNA of the host cell. Examples of integrase inhibitors include, without limitation, raltegravir, elvitegravir, GSK1265744 (cabotegravir), GSK1349572 (dolutegravir), GS-9883 (bictegravir), and MK-2048.

Anti-HIV compounds also include maturation inhibitors (e.g., bevirimat). Maturation inhibitors are typically compounds which bind HIV gag and disrupt its processing during the maturation of the virus. Anti-HIV compounds also include HIV vaccines such as, without limitation, ALVAC® HIV (vCP1521), AIDSVAX®B/E (gp120), and combinations thereof. Anti-HIV compounds also include HIV antibodies (e.g., antibodies against gp120 or gp41), particularly broadly neutralizing antibodies.

More than one anti-HIV agent may be used, particularly where the agents have different mechanisms of action (as outlined above). For example, anti-HIV agents which are not NRTIs may be combined with the NRTI prodrugs of the instant invention. In a particular embodiment, the anti-HIV therapy is highly active antiretroviral therapy (HAART).

The instant invention encompasses compositions (e.g., pharmaceutical compositions) comprising at least one prodrug and/or nanoparticle of the instant invention and at least one pharmaceutically acceptable carrier. As stated hereinabove, the nanoparticle may comprise more than one therapeutic agent. In a particular embodiment, the pharmaceutical composition comprises a first nanoparticle comprising a first prodrug and a second nanoparticle comprising a second prodrug, wherein the first and second prodrugs are different. The compositions (e.g., pharmaceutical compositions) of the instant invention may further comprise other therapeutic agents (e.g., other anti-HIV compounds (e.g., those described herein)).

The present invention also encompasses methods for preventing, inhibiting, and/or treating a disease or disorder. The methods comprise administering a prodrug and/or nanoparticle of the instant invention (optionally in a composition) to a subject in need thereof. In a particular embodiment, the disease or disorder is a microbial (e.g., viral) infection, cancer, or a blood clotting disorder (e.g., the prodrug or nanoparticle of the invention can be used as an antiplatelet drug to inhibit or prevent formation of a blood clot). Microbial infections include, without limitation, viral, bacterial, fungal, mycobacyterial and parasitic infections. In a particular embodiment, the disease or disorder is a viral infection. Examples of viral infections include, without limitation: HIV, Hepatitis B, Hepatitis C, Influenza A, Influenza B, Ebola, and Herpes Simplex. In a particular embodiment, the viral infection is a retroviral or lentiviral infection, particularly an HIV infection (e.g., HIV-1). In a particular embodiment, the cancer includes, but is not limited to, leukemia (e.g., acute lymphoblastic leukemia, acute myeloid leukemia, chronic lymphocytic leukemia, chronic myelogenous leukemia), lymphoma (e.g., Hodgkin lymphoma, Non-Hodgkin lymphoma), multiple myeloma, breast cancer, prostate cancer, pancreatic cancer, colon cancer, thyroid cancer, bladder cancer, liver cancer, neuroblastoma, brain cancers (e.g., gliomas, meningiomas, and pituitary adenomas), lung cancer, ovarian cancer, stomach cancer, skin cancer (e.g., melanoma), cervical cancer, testicular cancer, kidney cancer, carcinoid tumors, and bone cancer.

The prodrugs and/or nanoparticles of the instant invention (optionally in a composition) can be administered to an animal, in particular a mammal, more particularly a human, in order to treat/inhibit/prevent the disease or disorder (e.g., an HIV infection). The pharmaceutical compositions of the instant invention may also comprise at least one other therapeutic agent such as an antiviral agent, particularly at least one other anti-HIV compound/agent. The additional anti-HIV compound may also be administered in a separate pharmaceutical composition from the prodrugs or compositions of the instant invention. The pharmaceutical compositions may be administered at the same time or at different times (e.g., sequentially).

The dosage ranges for the administration of the prodrugs, nanoparticles, and/or compositions of the invention are those large enough to produce the desired effect (e.g., curing, relieving, treating, and/or preventing the disease or disorder (e.g., HIV infection), the symptoms of it (e.g., AIDS, ARC), or the predisposition towards it). In a particular embodiment, the pharmaceutical composition of the instant invention is administered to the subject at an amount from about 5 µg/kg to about 500 mg/kg. In a particular embodiment, the pharmaceutical composition of the instant invention is administered to the subject at an amount greater than about 5 µg/kg, greater than about 50 µg/kg, greater than about 0.1 mg/kg, greater than about 0.5 mg/kg, greater than about 1 mg/kg, or greater than about 5 mg/kg. In a particular embodiment, the pharmaceutical composition of the instant invention is administered to the subject at an amount from about 0.5 mg/kg to about 100 mg/kg, about 10 mg/kg to about 100 mg/kg, or about 15 mg/kg to about 50 mg/kg. The dosage should not be so large as to cause significant adverse side effects, such as unwanted cross-reactions, anaphylactic reactions, and the like. Generally, the dosage will vary with the age, condition, sex and extent of the disease in the patient and can be determined by one of skill in the art. The dosage can be adjusted by the individual physician in the event of any counter indications.

The prodrugs and nanoparticles described herein will generally be administered to a patient as a pharmaceutical composition. The term "patient" as used herein refers to human or animal subjects. These prodrugs and nanoparticles may be employed therapeutically, under the guidance of a physician.

The pharmaceutical compositions comprising the prodrugs and/or nanoparticles of the instant invention may be conveniently formulated for administration with any pharmaceutically acceptable carrier(s). For example, the complexes may be formulated with an acceptable medium such as water, buffered saline, ethanol, polyol (for example, glycerol, propylene glycol, liquid polyethylene glycol and the like), dimethyl sulfoxide (DMSO), oils, detergents, suspending agents, or suitable mixtures thereof, particularly an aqueous solution. The concentration of the prodrugs and/or nanoparticles in the chosen medium may be varied and the medium may be chosen based on the desired route of administration of the pharmaceutical composition. Except insofar as any conventional media or agent is incompatible with the nanoparticles to be administered, its use in the pharmaceutical composition is contemplated.

The dose and dosage regimen of prodrugs and/or nanoparticles according to the invention that are suitable for administration to a particular patient may be determined by a physician considering the patient's age, sex, weight, general medical condition, and the specific condition for which the nanoparticles are being administered and the severity thereof. The physician may also take into account the route of administration, the pharmaceutical carrier, and the nanoparticle's biological activity.

Selection of a suitable pharmaceutical composition will also depend upon the mode of administration chosen. For example, the nanoparticles of the invention may be administered by direct injection or intravenously. In this instance, a pharmaceutical composition comprises the prodrug and/or nanoparticle dispersed in a medium that is compatible with the site of injection.

Prodrugs and/or nanoparticles of the instant invention may be administered by any method. For example, the prodrugs and/or nanoparticles of the instant invention can be administered, without limitation parenterally, subcutaneously, orally, topically, pulmonarily, rectally, vaginally, intravenously, intraperitoneally, intrathecally, intracerbrally, epidurally, intramuscularly, intradermally, or intracarotidly. In a particular embodiment, the prodrug and/or nanoparticle is parenterally. In a particular embodiment, the prodrug and/or nanoparticle is administered intramuscularly, subcutaneously, or to the bloodstream (e.g., intravenously). Pharmaceutical compositions for injection are known in the art. If injection is selected as a method for administering the prodrug and/or nanoparticle, steps must be taken to ensure that sufficient amounts of the molecules or cells reach their target cells to exert a biological effect. Dosage forms for oral administration include, without limitation, tablets (e.g., coated and uncoated, chewable), gelatin capsules (e.g., soft or hard), lozenges, troches, solutions, emulsions, suspensions, syrups, elixirs, powders/granules (e.g., reconstitutable or dispersible) gums, and effervescent tablets. Dosage forms for parenteral administration include, without limitation, solutions, emulsions, suspensions, dispersions and powders/granules for reconstitution. Dosage forms for topical administration include, without limitation, creams, gels, ointments, salves, patches and transdermal delivery systems.

Pharmaceutical compositions containing a prodrug and/or nanoparticle of the present invention as the active ingredient in intimate admixture with a pharmaceutically acceptable carrier can be prepared according to conventional pharmaceutical compounding techniques. The carrier may take a wide variety of forms depending on the form of pharmaceutical composition desired for administration, e.g., intravenous, oral, direct injection, intracranial, and intravitreal.

A pharmaceutical composition of the invention may be formulated in dosage unit form for ease of administration and uniformity of dosage. Dosage unit form, as used herein, refers to a physically discrete unit of the pharmaceutical composition appropriate for the patient undergoing treatment. Each dosage should contain a quantity of active ingredient calculated to produce the desired effect in association with the selected pharmaceutical carrier. Procedures for determining the appropriate dosage unit are well known to those skilled in the art. In a particular embodiment, the prodrugs and/or nanoparticles of the instant invention, due to their long-acting therapeutic effect, may be administered once every 1 to 12 months or even less frequently. For example, the nanoformulations of the instant invention may be administered once every 0.5, 1, 2, 3, 4, 5, 6, 7, 8, 9, 10, 11, 12, 15, 18, 21, 24, or more months.

Dosage units may be proportionately increased or decreased based on the weight of the patient. Appropriate concentrations for alleviation of a particular pathological condition may be determined by dosage concentration curve calculations, as known in the art.

In accordance with the present invention, the appropriate dosage unit for the administration of nanoparticles may be determined by evaluating the toxicity of the molecules or cells in animal models. Various concentrations of nanoparticles in pharmaceutical composition may be administered to mice, and the minimal and maximal dosages may be determined based on the beneficial results and side effects observed as a result of the treatment. Appropriate dosage unit may also be determined by assessing the efficacy of the nanoparticle treatment in combination with other standard drugs. The dosage units of nanoparticle may be determined individually or in combination with each treatment according to the effect detected.

The pharmaceutical composition comprising the nanoparticles may be administered at appropriate intervals until the pathological symptoms are reduced or alleviated, after which the dosage may be reduced to a maintenance level. The appropriate interval in a particular case would normally depend on the condition of the patient.

The instant invention encompasses methods of treating a disease/disorder comprising administering to a subject in need thereof a pharmaceutical composition comprising a prodrug and/or nanoparticle of the instant invention and, preferably, at least one pharmaceutically acceptable carrier. The instant invention also encompasses methods wherein the subject is treated via ex vivo therapy. In particular, the method comprises removing cells from the subject, exposing/contacting the cells in vitro to the nanoparticles of the instant invention, and returning the cells to the subject. In a particular embodiment, the cells comprise macrophage. Other methods of treating the disease or disorder may be combined with the methods of the instant invention may be co-administered with the pharmaceutical compositions of the instant invention.

The instant also encompasses delivering the nanoparticle of the instant invention to a cell in vitro (e.g., in culture). The nanoparticle may be delivered to the cell in at least one carrier.

Definitions

The following definitions are provided to facilitate an understanding of the present invention.

The singular forms "a," "an," and "the" include plural referents unless the context clearly dictates otherwise.

"Pharmaceutically acceptable" indicates approval by a regulatory agency of the Federal or a state government or listed in the U.S. Pharmacopeia or other generally recognized pharmacopeia for use in animals, and more particularly in humans.

A "carrier" refers to, for example, a diluent, adjuvant, preservative (e.g., Thimersol, benzyl alcohol), anti-oxidant (e.g., ascorbic acid, sodium metabisulfite), solubilizer (e.g., polysorbate 80), emulsifier, buffer (e.g., Tris HCl, acetate, phosphate), antimicrobial, bulking substance (e.g., lactose, mannitol), excipient, auxiliary agent or vehicle with which an active agent of the present invention is administered. Pharmaceutically acceptable carriers can be sterile liquids, such as water and oils, including those of petroleum, animal, vegetable or synthetic origin. Water or aqueous saline solutions and aqueous dextrose and glycerol solutions are preferably employed as carriers, particularly for injectable solutions. Suitable pharmaceutical carriers are described in "Remington's Pharmaceutical Sciences" by E. W. Martin (Mack Publishing Co., Easton, Pa.); Gennaro, A. R., Remington: The Science and Practice of Pharmacy, (Lippincott, Williams and Wilkins); Liberman, et al., Eds., Pharmaceutical Dosage Forms, Marcel Decker, New York, N.Y.; and Kibbe, et al., Eds., Handbook of Pharmaceutical Excipients, American Pharmaceutical Association, Washington.

The term "prodrug" refers to a compound that is metabolized or otherwise converted to a biologically active or more active compound or drug, typically after administration. A prodrug, relative to the drug, is modified chemically in a manner that renders it, relative to the drug, less active, essentially inactive, or inactive. However, the chemical modification is such that the corresponding drug is generated by metabolic or other biological processes, typically after the prodrug is administered.

The term "treat" as used herein refers to any type of treatment that imparts a benefit to a patient afflicted with a disease, including improvement in the condition of the patient (e.g., in one or more symptoms), delay in the progression of the condition, etc. In a particular embodiment, the treatment of a retroviral infection results in at least an inhibition/reduction in the number of infected cells and/or detectable viral levels.

As used herein, the term "prevent" refers to the prophylactic treatment of a subject who is at risk of developing a condition (e.g., HIV infection) resulting in a decrease in the probability that the subject will develop the condition.

A "therapeutically effective amount" of a compound or a pharmaceutical composition refers to an amount effective to prevent, inhibit, treat, or lessen the symptoms of a particular disorder or disease. The treatment of a microbial infection (e.g., HIV infection) herein may refer to curing, relieving, and/or preventing the microbial infection, the symptom(s) of it, or the predisposition towards it.

As used herein, the term "therapeutic agent" refers to a chemical compound or biological molecule including, without limitation, nucleic acids, peptides, proteins, and antibodies that can be used to treat a condition, disease, or disorder or reduce the symptoms of the condition, disease, or disorder.

As used herein, the term "small molecule" refers to a substance or compound that has a relatively low molecular weight (e.g., less than 4,000, less than 2,000, particularly less than 1 kDa or 800 Da). Typically, small molecules are organic, but are not proteins, polypeptides, or nucleic acids, though they may be amino acids or dipeptides.

The term "antimicrobials" as used herein indicates a substance that kills or inhibits the growth of microorganisms such as bacteria, fungi, viruses, or protozoans.

As used herein, the term "antiviral" refers to a substance that destroys a virus and/or suppresses replication (reproduction) of the virus. For example, an antiviral may inhibit and or prevent: production of viral particles, maturation of viral particles, viral attachment, viral uptake into cells, viral assembly, viral release/budding, viral integration, etc.

As used herein, the term "highly active antiretroviral therapy" (HAART) refers to HIV therapy with various combinations of therapeutics such as nucleoside reverse transcriptase inhibitors, non-nucleoside reverse transcriptase inhibitors, HIV protease inhibitors, and fusion inhibitors.

As used herein, the term "amphiphilic" means the ability to dissolve in both water and lipids/apolar environments. Typically, an amphiphilic compound comprises a hydrophilic portion and a hydrophobic portion. "Hydrophobic" designates a preference for apolar environments (e.g., a hydrophobic substance or moiety is more readily dissolved in or wetted by non-polar solvents, such as hydrocarbons, than by water). "Hydrophobic" compounds are, for the most part, insoluble in water. As used herein, the term "hydrophilic" means the ability to dissolve in water.

As used herein, the term "polymer" denotes molecules formed from the chemical union of two or more repeating units or monomers. The term "block copolymer" most simply refers to conjugates of at least two different polymer segments, wherein each polymer segment comprises two or more adjacent units of the same kind.

An "antibody" or "antibody molecule" is any immunoglobulin, including antibodies and fragments thereof (e.g., scFv), that binds to a specific antigen. As used herein, antibody or antibody molecule contemplates intact immunoglobulin molecules, immunologically active portions of an immunoglobulin molecule, and fusions of immunologically active portions of an immunoglobulin molecule.

As used herein, the term "immunologically specific" refers to proteins/polypeptides, particularly antibodies, that bind to one or more epitopes of a protein or compound of interest, but which do not substantially recognize and bind other molecules in a sample containing a mixed population of antigenic biological molecules.

As used herein, the term "targeting ligand" refers to any compound which specifically binds to a specific type of tissue or cell type, particularly without substantially binding other types of tissues or cell types. Examples of targeting ligands include, without limitation: proteins, polypeptides, peptides, antibodies, antibody fragments, hormones, ligands, carbohydrates, steroids, nucleic acid molecules, and polynucleotides.

The term "aliphatic" refers to a non-aromatic hydrocarbon-based moiety. Aliphatic compounds can be acyclic (e.g., linear or branched) or cyclic moieties (e.g., cycloalkyl) and can be saturated or unsaturated (e.g., alkyl, alkenyl, and alkynyl). Aliphatic compounds may comprise a mostly carbon main chain (e.g., 1 to about 30 carbons) and comprise heteroatoms and/or substituents (see below). The term "alkyl," as employed herein, includes saturated or unsaturated, straight or branched chain hydrocarbons containing 1 to about 30 carbons in the normal/main chain. The hydrocarbon chain of the alkyl groups may be interrupted with one or more heteroatom (e.g., oxygen, nitrogen, or sulfur). An alkyl (or aliphatic) may, optionally, be substituted (e.g. with fewer than about 8, fewer than about 6, or 1 to about 4 substituents). The term "lower alkyl" or "lower aliphatic" refers to an alkyl or aliphatic, respectively, which contains 1 to 3 carbons in the hydrocarbon chain. Alkyl or aliphatic substituents include, without limitation, alkyl (e.g., lower alkyl), alkenyl, halo (such as F, Cl, Br, I), haloalkyl (e.g., $CCl_3$ or $CF_3$), alkoxyl, alkylthio, hydroxy, methoxy, carboxyl, oxo, epoxy, alkyloxycarbonyl, alkylcarbonyloxy, amino, carbamoyl (e.g., $NH_2C(=O)-$ or $NHRC(=O)-$, wherein R is an alkyl), urea ($-NHCONH_2$), alkylurea, aryl, ether, ester, thioester, nitrile, nitro, amide, carbonyl, carboxylate and thiol. Aliphatic and alkyl groups having at least about 5 carbons in the main chain are generally hydrophobic, absent extensive substitutions with hydrophilic substituents.

The term "aryl," as employed herein, refers to monocyclic and bicyclic aromatic groups containing 6 to 10 carbons in the ring portion. Examples of aryl groups include, without limitation, phenyl or naphthyl, such as 1-naphthyl and 2-naphthyl, or indenyl. Aryl groups may optionally include one to three additional rings fused to a cycloalkyl ring or a heterocyclic ring. Aryl groups may be optionally substituted through available carbon atoms with, for example, 1, 2, or 3 groups selected from hydrogen, halo, alkyl, polyhaloalkyl, alkoxy, alkenyl, trifluoromethyl, trifluoromethoxy, alkynyl, aryl, heterocyclo, aralkyl, aryloxy, aryloxyalkyl, aralkoxy, arylthio, arylazo, heterocyclooxy, hydroxy, nitro, cyano, sulfonyl anion, amino, or substituted amino. The aryl group may be a heteroaryl. "Heteroaryl" refers to an optionally substituted, mono-, di-, tri-, or other multicyclic aromatic ring system that includes at least one, and preferably from 1 to about 4, sulfur, oxygen, or nitrogen heteroatom ring members. Heteroaryl groups can have, for example, from about 3 to about 50 carbon atoms (and all combinations and subcombinations of ranges and specific numbers of carbon atoms therein), with from about 4 to about 10 carbons being preferred.

The following examples provide illustrative methods of practicing the instant invention and are not intended to limit the scope of the invention in any way.

Example 1

The translation of long acting slow effective release antiretroviral therapy (LASER ART) from laboratory research into clinical practice could improve human immunodeficiency virus (HIV) prevention and treatment and inevitably speed up viral eradication efforts. The advantages of LASER ART over other antiretroviral regimens are defined by high antiretroviral drug (ARV) penetrance into cell and tissue viral reservoirs and infrequent dosing requirements. Both affect treatment outcomes by maximally suppressing viral growth through facilitated ARV entry into viral target cells (Edagwa, et al., Expert Opin. Drug Deliv. (2017) 14:1281-1291; Landovitz, et al., Curr. Opin. HIV AIDS (2016) 11:122-128). Regimen adherence can be improved by reducing the dosing frequency. Indeed, recent data demonstrate that conversion of existing ARVs into prodrugs extends their apparent half-lives and reduces systemic drug toxicities (Sillman, et al., Nat. Commun. (2018) 9:443; Zhou, et al., Biomaterials (2018) 151:53-65; Singh, et al., Nanomedicine (2016) 11:1913-1927; Guo, et al., J. Acquired Immune Defic. Syndr. (2017) 74:e75-e83). However, while prodrugs represent >10% of all small molecules approved for human use, few have entered into HIV treatment regimens and none have appeared as part of long-acting ARV therapies (Rautio, et al., Nat. Rev. Drug Discov. (2018) 17(8):559-587). Nonetheless, their advantages in facilitating drug biodistribution and extending drug half-lives is clear (Huttunen, et al., Pharmacol. Rev. (2011) 63:750-771).

The application of targeted phosphoramidate pronucleotides (ProTides) to create prodrugs of established antiretrovirals and transform them into long acting slow effective release antiretroviral therapies (LASER ART) encased in nanoparticles are provided. Methods for the synthesis of the LASER ART ProTides (LASER PROART) are described for abacavir (ABC), lamivudine (3TC), emtricitabine (FTC) and tenofovir (TFV). However, these methods are readily applicable to other therapeutic agents such as anti-virals and cancer drugs.

The prodrugs described herein contain a long chain fatty alcohol at position $R_1$. This linkage affects drug lipophilicity and improves antiretroviral potency. Further, the placement of a bulky group at $R_1$ did not compromise potency. The prodrugs were prepared by a Grignard-mediated phosphorochloridate reaction. The resultant prodrugs demonstrated improved antiretroviral activities when compared to native drugs or myristolyated prodrugs. Modifications of the aryl, ester, and amino acid regions of the ProTide affect the metabolic stability and create a hydrophobic, lipophilic nanocrystal. The resultant particle has in its core nucleoside and nucleotide monophosphate analogs masked with aryls and amino acid esters with active fatty alcohols. The nanoformulated antiretroviral prodrugs (including, without limitation, NPABC, NP3TC, NPFTC and NPTFV) show enhanced antiretroviral responses, increased cellular and tissue penetration and extended half-lives when compared to their native drugs or myristolyated prodrugs or nanoformulated nucleosides. The nanoformulated ProTide LASER ART (LASER PROART) presented herein and their combinations can be used in the management of HIV/AIDS.

Methods

Chemicals and Reagents

All chemical synthesis reactions were performed under a dry argon atmosphere unless otherwise noted. Reagents were obtained from commercial sources and used directly; exceptions are noted. Abacavir was purchased from BOC Sciences Inc. (Shirley, N.Y.). Phenyl dichlorophosphate, L-alanine methyl ester hydrochloride salt, L-phenylalanine methyl ester hydrochloride salt, N-(carbobenzyloxy)-L-phenylaline, docosanol, dichloromethane ($CH_2Cl_2$), chloroform ($CHCl_3$), N,Ndimethylformamide (DMF), triethylamine ($Et_3N$), diethyl ether, tetrahydrofuran (THF), tert-Butylmagnesium chloride solution (tert-BuMgCl, 1.0M in THF), triethylsilane ($Et_3SiH$), methanol and poly (D, L-lactide-co-glycolide; lactide:glycolide (75:25), mol. wt. 66,000-107,000) (PLGA) were purchased from Sigma-Aldrich (St. Louis, Mo.). Distearoyl-phosphatidylethanolamine-methyl-polyethylene glycol conjugate-2000 (DSPE-mPEG2k), 1,2-distearoyl-sn-glycero-3-phosphocholine (DSPC) and 1,2-distearoyl-sn-glycero-3-phosphoglycerol (DSPG) were purchased from Corden Pharma (Cambridge, Mass.). 1-[Bis (dimethylamino) methylene]-1H-1,2,3-triazolo[4,5-b] pyridinium 3-oxidhexafluorophosphate (HATU) was obtained from Bachem Inc. (Torrance, Calif.) while palladium, 10% on activated carbon, was purchased from STREM Inc. (Newburyport, Mass.). Flash chromatography was performed using flash silica gel (32-63µ) from SiliCycle Inc. (Quebec, Canada). Chemical reactions were analyzed by thin layer chromatography (TLC) on precoated silica plates (200 µm, F-254) from Sorbtech technologies Inc. (Norcross, Ga.). The compounds were visualized by UV fluorescence or by staining with ninhydrin or $KMnO_4$ reagents.

High Performance Liquid Chromatography (HPLC)

Prodrug quantitation was performed on a Waters® Breeze™ HPLC system (Waters, Milford, Mass.) using a Kinetex® 5µ C18 100 A Phenomenex column. HPLC grade acetonitrile and methanol were purchased from Fisher Chemical. For all three ProTide samples, 10 mM potassium phosphate monobasic buffer solution (10 mM $KH_2PO_4$) was used at a flow rate of 1 mL/minute. Specifically, M1ABC was eluted in 10 mM $KH_2PO_4$/acetonitrile (65/35, v/v) mobile phase with a retention time of 3.8 minutes; M2ABC had a retention time of 4.2 minutes in 10 mM $KH_2PO_4$/acetonitrile (55/45, v/v), while M3ABC had a retention time of 7.0 minutes in 10 mM $KH_2PO_4$/methanol (2/98, v/v).

Nuclear Magnetic Resonance (NMR)

NMR spectra were recorded on a Bruker Avance-III™ HD (Billerica, Mass.) operating at 500 MHz, a magnetic field strength of 11.7 T. Proton NMR data is reported in ppm downfield from TMS as an internal standard.

Mass Spectrometry (MS)

Mass spectra were obtained on a Waters Xevo® TQ-S micro triple quadrupole mass spectrometer (Waters, Milford, Mass.).

Fourier-Transform Infrared Spectroscopy (FTIR)

FTIR spectra were recorded on a Perkin-Elmer-spectrum attenuated total reflectance (ATR)-FTIR equipped with a UATR-accessary (Perkin-Elmer, Inc., Waltham, Mass.).

Synthesis and Characterization

Z-Phe-Odoc (2): Triethylamine (1.35 g, 1.86 mL, 13.36 mmol, 2.0 equiv.), imidazole (454 mg, 6.68 mmol, 1.0 equiv.) and HATU (3.81 g, 10.02 mmol, 1.5 equiv.) were added to a solution of Z-Phe-OH (2 g, 6.68 mmol, 1.0 equiv.) and docosanol (2.4 g, 7.35 mmol, 1.1 equiv.) in a mixture of $CHCl_3$ (25 mL) and DMF (25 mL) at 0° C. under an argon atmosphere. The mixture was then heated at 45° C. for 48 hours and concentrated. The crude product was diluted with $CH_2Cl_2$ (100 mL), washed successively with 1 M HCl, saturated $NaHCO_3$ and brine (80 mL each). The organic extract was dried over $Na_2SO_4$ and concentrated. The residue was purified by flash chromatography eluting with 4:1 Hex/EtOAc to give Z-Phe-Odoc (3.46 g, 85%) as a colorless solid. $^1$H NMR (500 MHz, $CD_3OD$): 7.24-7.42 (m, 9H), 7.13 (d, J=6.7 Hz, 2H), 5.25 (d, J=4.0 Hz, 1H), 5.07-5.17 (m, 1H), 4.68 (dd, J=13.6, 6.0 Hz 1H), 4.12 (td, J=13.6, 6.7 Hz 2H), 3.14 (m, 2H), 1.60 (br, 2H), 1.29 (br, 38H), 0.92 (t, J=6.9 Hz 3H). $^{13}$C NMR (125 MHz, $CDCl_3$): δ 171.6, 155.6, 136.2, 135.7, 129.2, 128.5, 128.4, 29.2, 28.4, 25.8, 22.7, 14.1. MS-ES+ (m/z): calcd. for $C_{39}H_{61}NO_4$, 607.46 (100%), 608.46 (42.2%), 609.47 (8.7%); found, 608.46 [M+H+].

H-Phe-Odoc (3c): To a solution of 2 (3.46 g, 5.695 mmol, 1.0 equiv.) in mixture of anhydrous MeOH (20 mL) and $CHCl_3$ (10 mL) was added Pd/C (1.4 g, 40% wt). The reaction mixture was cooled to 0° C. followed by drop wise addition of triethylsilane (6.6 g, 9.1 mL, 59.95 mmol, 10.0 equiv.) (Mandal, et al., J. Org. Chem. (2007) 72:6599-6601). The reaction mixture was then stirred under an atmosphere of argon at room temperature for 16 hours, filtered through Celite® and then concentrated to give H-Phe-Odoc (quantitative yield), that was precipitated from ether and used in the next step without further purification.

General Procedure A: Aryl aminoacyl phosphorochloridates (McGuigan, et al., J. Med. Chem. (2005) 48:3504-3515). The amino acid ester (1 mol equiv) and phenyl dichlorophosphate (1 mol equiv) were suspended in anhydrous $CH_2Cl_2$ (15 mL) and cooled to −78° C. in a dry ice/acetone bath. To this mixture, a pre-cooled (−78° C.) solution of anhydrous trimethylamine (2 mol equiv) in $CH_2Cl_2$ was added drop-wise, and the resultant solution was stirred and gradually warmed to room temperature over 32 hours under an inert argon atmosphere. The reaction mixture was concentrated on a rotary evaporator to yield a white solid that was suspended into diethyl ether and filtered. The filtrate was concentrated to give aryl aminoacyl phosphochloridates that were used in the next coupling step without further purification.

General Procedure B: Abacavir ProTides (McGuigan, et al., J. Med. Chem. (2005) 48:3504-3515). ABC (1 mol equiv) was dried by azeotroping from anhydrous pyridine, then suspended in anhydrous THF and cooled to −78° C. under an argon atmosphere. tert-Butylmagnesium chloride (2 mol equiv, 1.0 M solution in THF) was added drop wise to the ABC suspension and the reaction mixture allowed to stir for an additional 10 minutes with cooling. A solution of aminoacyl phosphorochloridate (1.5 mol equiv) in THF was then added drop-wise and the resulting mixture was gradually warmed to room temperature and stirred for 48-90 hours. The reaction mixture was then cooled to 0° C., quenched with aqueous saturated ammonium chloride solution or methanol, concentrated, and the desired ABC ProTides isolated by flash column chromatography on silica gel eluting with 95%-90% $CH_2Cl_2/CH_3OH$ mobile phase.

Preparation of M1ABC (5a): Synthesized according to general procedure B. On a scale of 1.0 g (3.49 mmol) of ABC, 1.4 g (2.66 mmol, 76% yield) of M1ABC product was formed: $^1H$ NMR (500 MHz, CD3OD): 7.66 (d, J=6.6 Hz 1H), 7.10-7.40 (m, 6H), 6.15 (dd, J=13.7, 5.7 Hz 1H), 5.97 (br, 1H), 5.53 (br, 1H), 4.08-4.30 (m, 2H), 3.85-4.0 (m, 1H), 3.23 (s, 3H), 3.21 (br, 1H), 2.93 (br, 1H), 2.81 (td, J=16.9, 8.3 Hz 1H), 1.65-1.80 (m, 1H), 1.20-1.40 (m, 4H), 0.85 (app. d, J=5.8 Hz 2H), 0.62 (br, 2H). $^{13}C$ NMR (125 MHz, $CDCl_3$): δ 175.4, 161.7, 157.4, 152.2, 138.1, 137.2, 131.7, 130.6, 126.1, 123.7, 121.4, 114.8, 70.1, 60.5, 52.7, 51.5, 47.1, 35.4, 24.3, 20.8, 20.5, 14.5, 7.6. $^{31}P$ NMR (202 MHz, $CD_3OD$); 3.87, 3.58. MSES+ (m/z): calcd. for $C_{24}H_{30}N_7O_5P$, 527.20 (100%), 528.21 (26.0%), 529.21 (2.7%); found, 528.2 [M+H+].

Preparation of M2ABC (5b): Synthesized according to general procedure B. On a scale of 1.6 g (5.59 mmol) of ABC, 1.9 g (3.15 mmol, 55% yield) of M2ABC was formed: $^1H$ NMR (500 MHz, $CD_3OD$): 7.59 (d, J=28 Hz 1H), 7.09-7.40 (m, 10H), 7.06 (d, J=7.6 Hz 1H), 6.01-6.08 (m, 1H), 5.87-5.95 (m, 1H), 5.43-5.53 (m, 1H), 4.15 (dd, J=14.8, 9.1 Hz 1H), 3.92-4.04 (m, 1H), 3.45-3.80 (m, 5H), 2.88-3.14 (m, 3H), 2.78-2.87 (m, 1H), 2.65-2.74 (m, 1H), 1.50-1.58 (m, 1H), 0.82-0.89 (m, 2H), 0.57-0.65 (m, 2H). $^{13}C$ NMR (125 MHz, $CDCl_3$): δ 174.5, 157.4, 152.2, 152.1, 151.6, 138.3, 138.1, 137.2, 131.5, 130.7, 130.6, 129.5, 127.9, 126.0, 125.9, 121.6, 121.1, 114.8, 69.8, 69.7, 60.4, 57.9, 57.7, 52.6, 46.8, 40.8, 35.4, 24.4, 7.6. $^{31}P$ NMR (202 MHz, $CD_3OD$); 3.62, 3.22. MS-ES+ (m/z): calcd. for $C_{30}H_{34}N_7O_5P$, 603.24 (100%), 604.24 (32.4%), 605.24 (2.4%); found, 604.24 [M+H+].

Preparation of M3ABC (5c): Synthesized according to general procedure B. On a scale of 1.1 g (3.84 mmol) of ABC, 2.4 g (2.64 mmol, 68% yield) of M3ABC product was formed: $^1H$ NMR (500 MHz, $CD_3OD$): 7.59 (d, J=28 Hz 1H), 6.95-7.44 (m, 11H), 6.04 (br, 1H), 5.88-5.95 (m, 1H), 5.48 (br, 1H), 4.13 (d, J=15.2, 8.7 Hz 1H), 3.89-4.09 (m, 3H), 3.47-3.59 (m, 2H), 2.64-3.15 (m, 5H), 1.45-1.64 (m, 3H), 1.07-1.39 (br, 42H), 0.91 (t, J=6.6 Hz 3H), 0.84-0.87 (m, 2H), 0.61 (br, 2H). $^{13}C$ NMR (125 MHz, $CD_3OD$): δ 174.2, 157.4, 154.3, 152.1, 144.9, 138.3, 138.2, 138.0, 137.9, 137.1, 131.5, 130.6, 130.5, 130.3, 130.1, 129.6, 128.9, 127.9, 126.7, 125.9, 124.1, 121.9, 121.4, 121.3, 121.1, 114.8, 69.9, 66.7, 66.4, 63.2, 60.4, 58.1, 57.8, 46.8, 41.1, 35.4, 33.1, 31.2, 30.7, 30.5, 29.6, 29.5, 26.9, 23.8, 14.5, 7.6; $^{31}P$ NMR (202 MHz, $CD_3OD$); 3.25, 3.54. MS-ES+(m/z): calcd. for $C_{51}H_{76}N_7O_5P$, 897.56 (100%), 898.57 (55.2%), 899.57 (14.9%); found, 898.56 [M+H+].

Cell model for in vitro studies: Human peripheral blood monocytes were obtained and cultured as described (Gendelman, et al., J. Exp. Med. (1988) 167:1428-1441). Briefly, human peripheral blood monocytes were obtained by leukapheresis from HIV-1/2 and hepatitis B seronegative donors, followed by purification via countercurrent centrifugal elutriation. Elutriated monocytes were cultured as adherent cells in Dulbecco's minimum essential medium (DMEM) supplemented with 10% heat-inactivated pooled human serum, 10 μg/mL ciprofloxacin, 50 μg/mL gentamicin, and 1000 U/mL recombinant macrophage colony stimulating factor. Cells were maintained at 37° C. in a 5% CO2 incubator. Seven days later, differentiated macrophages (MDM) were used for the experiments.

Antiretroviral activity of ABC and its ProTides: The antiviral activities of native ABC and ABC ProTides against HIV-1$_{ADA}$ were determined in MDM as described (Singh, et al., Nanomedicine (2016) 11:1913-1927). MDM were incubated with various concentrations of ABC or ABC ProTides for 60 minutes followed by infection with HIV-1$_{ADA}$ at a multiplicity of infection (MOI) of 0.01 for 4 hours. The MDM were washed extensively with phosphate buffered saline (PBS) to remove excess virus particles. The cells were incubated an additional 10 days in the presence of the same concentration of drug used before infection. Cell culture medium was changed every other day with replacement of equivalent drug containing media. At day 10 post infection, supernatants were collected and analyzed for HIV-1 reverse transcriptase (RT) activity (Kalter, et al., J. Clin. Microbiol. (1992) 30:993-995).

Intracellular level of CBV-TP of ABC and its ProTides: Intracellular levels of CBV-TP were measured as described (Balzarini, et al., FEBS Lett. (2004) 573:38-44). MDM were treated with 10 μM ABC and ABC ProTides. At 3, 6, 12, 24 and 48 hours after treatment, MDM were washed with PBS to remove excess free drug. The cells were then collected in 70% methanol. CBV-TP from MDM was extracted and quantitated by LC-MS/MS as described (Gautam, et al., J. Pharm. Biomed. Anal. (2018) 153:248-259). Sep-Pak QMA cartridges (360 mg, 37-55 μm; Waters) were used to separate CBV-TP from their mono- and di-phosphates counterparts. The QMA cartridges were conditioned with 10 ml of 500 mM KCl followed by 10 ml of 5 mM KCl. Samples were loaded onto the cartridges and washed with 15 ml of 75 mM KCl. The triphosphate fraction was eluted with 3 ml of 500 mM KCl and collected for de-phosphorylation. The pH of the TP fraction was lowered to 4.25 by adding 15 μl ammonium acetate buffer (pH 4.10 mM) per ml eluate, and dephosphorylated by adding one unit of type XA sweet potato acid phosphatase per ml eluate and incubating at 37° C. for 30 minutes. The $^{15}N_2^{13}C$-3TC and d$_4$-ABC internal standard was added at this point. Samples were then loaded onto Waters OASIS® HLB cartridges (60 mg, 30 µm; Waters) pre-conditioned with 3 ml MeOH and 3 ml $H_2O$, and washed with 3.5 ml $H_2O$ to remove salts. The nucleosides of interest were then eluted with 1.5 ml of MeOH and evaporated under vacuum. Once dry, the residue was reconstituted with a 100 µl of 25% MeOH and stored in the −20° C. freezer until the time of LC-MS/MS analyses. The LC-MS/MS system comprised of a Waters ACQUITY ultra-performance liquid chromatography (UPLC) system (Waters, Milford, Mass.) coupled to a triple quadrupole mass spectrometer with electrospray ionization (ESI) source (Waters Xevo TQ-XS). For the indirect quantification of TPs, chromatographic separation was performed with an ACQUITY UPLC using CSH analytical column (2.1×100 mm, 1.7 µm; Waters) equipped with a guard column (Waters, Milford, Mass.). Mobile phase A consisted of ammonium bicarbonate (pH 7, 7.5 mM) and mobile phase B was methanol. The flow rate was 0.25 ml/minute. The initial mobile phase composition was 12% B for the first 2.5 minutes, gradually increased to 30% B over 4 minutes, gradually increased again to 95% B over 3.5 minutes, and then held constant for one minute. Mobile phase B was then reset to 12% over 0.25 minutes and the column was equilibrated for 2.75 minutes before the next injection. The total run time was 13 minutes. The mass spectrometer was operated in the positive ion mode using multiple reaction monitoring (MRM). The following transitions were monitored: m/z 230→112 for 3TC, m/z 248→152 for CBV, m/z 287→191 for ABC, m/z 233→115 for the internal standard (IS) $^{15}N_2{}^{13}C$-3TC, and m/z 291→195 for IS $d_4$-ABC. 3TC, CBV, ABC, $^{15}N_2{}^{13}C$-3TC, and $d_4$-ABC were detected at a cone voltage of 22, 2, 4, 12, and 2 V, respectively, and a collision energy of 12, 12, 20, 10, and 20 V, respectively.

Cell viability of ABC and its ProTides: A CCK-8 Kit was purchased from Dojindo (Rockville, Md.) and used to test cell viability after treatment with ABC and its ProTides. Briefly, MDM plated in a 96-well plate were treated with 100 µl of 0-400 µM ABC and its ProTides for 24 hours. Drug containing medium was removed and replaced with fresh medium. Ten µl of CCK-8 solution was added to each well followed by incubation of the plate for 2 hours at 37° C. The absorbance (at 450 nm) of each well was measured using a microplate reader. The cell viability was calculated according to manufacturer's instructions.

Stability Assay in Serum: The experiment was carried out by adding each ProTide into 100 µl human serum to reach a final concentration of 15 µg/ml in glass vial, and duplicate samples were used for each ProTide. After incubating the samples at 37° C. with shaking for 24 hours, 900 µl of MeOH was added to stop the reaction. Samples were vortexed for 3 minutes, then centrifuged down at 16,000 g for 10 minutes. The supernatants were transfer to new 2 ml tubes and evaporated to dryness under vacuum. The samples were reconstituted using 50 µl of MeOH, vortexed for 3 minutes and centrifuged down at 16,000 g for 10 minutes. The supernatants were analyzed by HPLC for drug concentrations. For control sample (0 minute), MeOH were added first to stop the enzyme before adding the ProTides.

Preparation and characterization of ABC phosphoramidate prodrug nanoformulations: Lipid-PLGA hybrid nanoparticles loaded with M1ABC (NM1ABC) were prepared using a modified single emulsion solvent evaporation technique as described (Liu, et al., Biomaterials (2010) 31:330-338). Briefly, a mixture of lipids consisting of DSPC, DSPE-PEG$_{2k}$ and DSPG in 10:5:1 weight ratio was coated over drug loaded PLGA nanoparticles to enable sustained release of the loaded cargo. A 2:1 weight ratio of PLGA core to lipid shell was used. NM2ABC and NM3ABC were prepared by high-pressure homogenization (Avestin EmulsiFlex-C3; Avestin Inc., Ottawa, ON, Canada) as described (Guo et al., J. Acquir. Immune Defic. Syndr. (2017) 74(3): e75-e83). Briefly, M2ABC or M3ABC (1% w/v) and poloxamer 407 (P407, 0.2% w/v) were premixed at room temperature overnight followed by homogenization at 20,000 psi until the desired particle size and polydispersity index (PdI) were achieved. Effective diameter (Deff), PdI, and potential were measured by dynamic light scattering (DLS) (Malvern Zetasizer Nano Series Nano-ZS, Malvern Instruments, Westborough, Mass.).

Cell uptake and retention of ABC phosphoramidate prodrug nanoformulations: Uptake and retention of nanoformulations were determined in MDM as described (Singh, et al., Nanomedicine (2016) 11:1913-1927; Sillman, et al., Nature Comm., (2018) 9:443; Zhou, et al., Biomaterials (2018) 151:53-65; Guo et al., J. Acquir. Immune Defic. Syndr. (2017) 74(3):e75-e83; Zhou et al., Nanomedicine (2018) 13(8):871-885). Briefly, MDM were treated with different nanoformulations at a concentration of 100 µM for 1, 2, 4 and 8 hours. At select time points, adherent MDM were collected in 1 mL PBS after washing with 1 mL PBS twice. MDM were pelleted by centrifugation at 3,000 rpm for 8 minutes. The cell pellet was reconstituted in 200 µl methanol and probe sonication (10 seconds) was used to break the cells and extract drugs. After probe sonication, cell debris was pelleted by centrifugation at 14,000 rpm for 10 minutes and 4° C. The supernatant was analyzed for prodrug level using HPLC-UV/Vis. For retention, MDM were treated with 100 µM different nanoformulations for 8 hours. The nanoformulation-containing media were replaced with fresh media after washing MDM with PBS twice. At days 1, 5, 10, 15, 20, 25 and 30, MDM were collected in 1 mL PBS after washing with 1 mL PBS twice. The samples were processed as described above for analysis using HPLC. Intracellular CBV-TP levels were also measured for as an indicator of cell uptake and retention. Briefly, cells were scraped into PBS, pelleted by centrifugation at 3,000 rpm for 8 minutes, and reconstituted in 200 µl 70% methanol. CBV-TP was extracted, and the samples were analyzed by LC-MS/MS as described (Gautam, et al., J. Pharm. Biomed. Anal. (2018) 153:248-259).

Antiretroviral efficacy of nanoformulations: Antiviral efficacies of ABC and the ProTide nanoformulations in MDM were assessed as described (Singh, et al., Nanomedicine (2016) 11:1913-1927). MDM were treated with 100 µM different nanoformulations for 8 hours. Then nanoformulation-containing medium was replaced with fresh medium after washing MDM with PBS twice. Half media changes were conducted every other day. At predetermined time points, days 1, 5, 10, 15, 20, 25 and 30, MDM were infected with HIV-1$_{ADA}$ for 4 hours at a MOI of 0.1 and cultured with every-other-day half media changes for an additional 10 days. At day 10, supernatant was collected for RT assay and MDM were fixed with paraformaldehyde and immunostained for expression of HIVp24. Untreated, uninfected MDM served as negative controls (control), while MDM exposed to HIV-1$_{ADA}$ but not treated with nanoformulations, served as positive controls (HIV-1). For NM3ABC, a concentration response study was also conducted. MDM were treated with 1, 10, 25, 50 or 100 µM NM3ABC for 8 hours. The treated MDM were then washed twice with PBS. MDM were cultured for an additional 30 days in fresh media with half media changes every other day. At day 30, MDM were challenged with HIV-1$_{ADA}$ at a MOI of 0.1 for 4 hours. Excess virus was washed out with PBS and MDM were cultured for another 10 days. At day 10 post-exposure, media were collected for RT assay and MDM were fixed and immunostained for expression of HIVp24 antigen.

In vivo study with rats: Animal PK studies were conducted in accordance with the University of Nebraska Medical Center Institutional Animal Care and Use Committee. Male Sprague Dawley rat (250 g; Jackson Labs, Bar Harbor, Me.) were injected with NM3ABC (45 mg/kg ABC-eq.) intramuscularly (IM; caudal thigh muscle). Whole blood samples were collected at 2, 24 and 168 hours after injection. PBMC were separated from whole blood samples using HISTOPAQUE 1083 (Sigma #1083-1) following manufacturer's instruction. CBV-TP were extracted and quantified as described above.

Results

Herein, ABC prodrugs were successfully developed by PROdrug and nucleoTIDE (ProTide) technology. The application of ProTide technology to abacavir (ABC) has focused on improving drug potency (Balzarini, et al., FEBS Lett. (2004) 573:38-44; McGuigan, et al., J. Med. Chem. (2005) 48:3504-3515), but not on extending its apparent half-life or on affecting viral reservoir biodistribution. To these ends, strategies were implemented to mask parent drug monophosphates with cleavable hydrophobic lipids creating ProTides that demonstrated improved plasma drug stability, membrane penetration and encapsulation. The synthesis and antiretroviral profiles of three ABC ProTides are described. One, M3ABC, was defined by efficient encasement into nanoparticles, production of high intracellular carbovir-triphosphate (CBV-TP) metabolites and superior monocyte-macrophage depot formation that enhanced antiretroviral activities.

L-alanine and L-phenylalanine ester phosphoramidates provide potent ProTides (McGuigan, et al., J. Med. Chem. (2005) 48:3504-3515; McGuigan, et al., Antiviral Res. (1991) 15:255-263). Thus, M1ABC and M2ABC were created bearing alanine and phenylalanine methyl ester residues (FIG. 1A and FIG. 1E). M3ABC was synthesized by substituting the methyl ester in M2ABC for a docosyl ester promoiety. A docosanol masking ester motif was selected based on its lipophilicity, antiviral activities and inherent synergistic effect on nucleoside analogs (Katz, et al., Ann. N.Y. Acad. Sci. (1994) 724:472-488; Marcelletti, J. F., Antiviral Res. (2002) 56:153-166). ProTide hydrolysis was reasoned to release two pharmacophores that inhibit viral reverse transcriptase activity (Piantadosi, et al., J. Med. Chem. (1991) 34:1408-1414). Improving ABC physicochemical features should facilitate nanoformulation preparation, enhance intracellular ABC levels and extend the drugs' apparent half-life. The first step in the synthesis of ABC ProTides required preparation of aryl amino ester phosphorochloridates from appropriate amino acid esters and commercially available phenyl phosphorodichloridate (Cahard, et al., Mini-Rev. Med. Chem. (2004) 4:371-381). Phenylalanine and alanine methyl esters were purchased while phenylalanine docosyl ester was prepared according to step 1 of FIG. 1E. The aryl amino ester phosphorochloridates were then synthesized by coupling phenyl phosphorodichloridates to amino acid esters in the presence of triethylamine (FIG. 1E, Step 2) (McGuigan, et al., J. Med. Chem. (2005) 48:3504-3515). Each of the amino ester phosphorochloridates was then reacted with ABC in the presence of tert-butylmagnesium chloride and purified by flash column chromatography. This generated high yields of M1ABC, M2ABC and M3ABC (FIG. 1E, Step 3; FIG. 1A). Successful synthesis of ABC ProTides was confirmed by $^1$H, $^{13}$C and $^{31}$P NMR spectra. As reported for similar compounds, splitting of the peaks in the spectra of ProTides was associated with the co-existence of two stereoisomers at the phosphorus atom (Kandil, et al. Bioorg. Med. Chem. Lett. (2016) 26:5618-5623).

The ProTides were then evaluated for antiretroviral activity. As shown in FIG. 1B, M1ABC, M2ABC, and M3ABC exhibited a 6- to 200-fold increase in antiretroviral activity over ABC in human monocyte-derived macrophages (MDMs). M2ABC demonstrated the lowest $EC_{50}$ of 0.2 nM. The $EC_{50}$ of M1ABC and M3ABC were 1.8 nM and 7.0 nM, respectively. The differences were likely linked to rapid prodrug uptake and metabolism of M2ABC to form CBV-TP in MDM (Hanson, et al., Proc. Natl. Acad. Sci. (1990) 87:960-963; Birkus, et al., Mol. Pharmacol. (2008) 74:92-100). Activation of ABC ProTides requires intracellular processing to generate CBV-TP (McGuigan, et al., J. Med. Chem. (2005) 48:3504-3515). To better explain the differences in $EC_{50}$ between native ProTides and ABC, MDMs were exposed to equivalent concentrations of ABC, M1ABC, M2ABC, or M3ABC followed by quantitation of CBV-TP levels at multiple time points (Balzarini, et al., FEBS Lett. (2004) 573:38-44). As shown in FIG. 1C, the maximum CBV-TP levels for ABC, M1ABC, M2ABC, and M3ABC were 177, 35650, 33135 and 541 fmol per million cells, respectively. At 48 hours, the CBV-TP levels were 33, 789, 5025 and 230 fmol per million cells for ABC, M1ABC, M2ABC, and M3ABC. The differences in active metabolite levels further suggest that the three ProTides are rapidly taken up by MDMs but metabolized at rates dependent on amino acid ester hydrolysis. Notably, at 48 hours, the CBV-TP levels for M3ABC declined only by 57% compared to 81, 97 and 84% in the amount of active metabolite for ABC, M1ABC, and M2ABC (FIG. 1F). The enhanced lipophilicity and slower hydrolysis of M3ABC provides controlled and extended release of CBV-TP.

As intracellular nucleoside triphosphate levels have been implicated in drug toxicities (Kakuda, T. N., Clin. Ther. (2000) 22:685-708), the mitochondrial dehydrogenase activity of the ProTides was assessed using a CCK-8 assay. As shown in FIG. 1D, neither ABC, M1ABC, M2ABC, nor M3ABC affected cell viability at drug concentrations of up to 300 μM. However, differences in mitochondrial activity were seen at 400 μM with M1ABC and M2ABC compared to ABC. No significant differences were observed between M3ABC and ABC across all tested drug concentrations. These data indicated that the sustained release of an effective inhibitory concentration of CBV-TP from M3ABC was not detrimental to cell viability and suggested that M3ABC could be translated for human use. Previous studies have shown that in vivo accumulation of nucleoside triphosphates inside cells could be facilitated by prodrugs that exhibit greater stability in plasma (Lee, et al., Antimicrob. Agents Chemother. (2005) 49:1898-1906; Mackman, et al., Bioorg. Med. Chem. (2010) 18:3606-3617). To evaluate prodrug stability, three ProTides were incubated in human serum. After 24 hours, >60% of M1ABC and M2ABC was hydrolyzed. Nineteen percent of M3ABC, in contrast, was degraded after 24 hours.

LASER ART was developed to improve therapeutic and prophylactic outcomes for HIV/AIDS. In the first phase this was accomplished by formulating myristoylated prodrugs encased in a poloxamer surfactant (Sillman, et al., Nat. Commun. (2018) 9:443; Zhou, et al., Biomaterials (2018) 151:53-65; Singh, et al., Nanomedicine (2016) 11:1913-1927; Guo, et al., J. Acquired Immune Defic. Syndr. (2017) 74:e75-e83). For ABC, such modifications provided only low levels of CBV-TP for less than two weeks (Singh, et al., Nanomedicine (2016) 11:1913-1927; Gautam, et al., J. Pharm. Biomed. Anal. (2018) 153:248-259). ABC ProTide nanoformulations should produce higher levels of intracellular CBV-TP at substantially reduced dosing frequency. The less hydrophobic M1ABC was encapsulated into lipid-coated poly lactic-co-glycolic acid (PLGA) nanoparticles (NM1ABC) by a modified single emulsion solvent evaporation method while hydrophobic and lipophilic M2ABC and M3ABC ProTides were stabilized into poloxamer coated drug nanoparticles (NM2ABC and NM3ABC) by high-pressure homogenization (Zhou, et al., Nanomedicine (2018) 13:871-885; Liu, et al., Biomaterials (2010) 31:330-338; Lin and Gendelman, in *Encyclopedia of AIDS*, eds. Hope, et al., Springer New York, N.Y., N.Y., 2016, pp. 1-10). The directive of both schemes was to produce controlled release drug delivery systems. The drug loadings for the NM1ABC, NM2ABC and NM3ABC nanoparticles were 3, 43, and 47%, respectively, underlying the differences between PLGA and poloxamer drug encasement systems. Indeed, unlike high-pressure homogenization that produces nanoparticles stabilized by surfactants with high drug loading, PLGA nanoparticles exhibit low drug loading (Zhou, et al., Nanomedicine (2018) 13:871-885; Xu, et al., Sci. Rep. (2017) 7:4794). Effective diameter ($D_{eff}$), polydispersity index (PdI), and $\zeta$-potential were determined by dynamic light scattering (DLS) (Table 1) while transmission electron microscopy (TEM) assessed nanoparticle morphologies. The nanoparticle morphologies for NM1ABC and NM3ABC were spherical with particle sizes of 135 nm and 230 nm, respectively, while NM2ABC particles were rod-shaped with a size of 265 nm. Importantly, high drug loading in NM2ABC and NM3ABC nanoformulations can translate into reduced dosage volumes and minimal injection site reactions (Lin and Gendelman, in *Encyclopedia of AIDS*, eds. Hope, et al., Springer New York, N.Y., N.Y., 2016, pp. 1-10).

TABLE 1

| Name | $D_{eff}$ (nm) | PdI | $\zeta$-potential (mV) | Drug loading (%) |
|---|---|---|---|---|
| NM1ABC | 237 ± 2 | 0.15 ± 0.03 | −43.4 ± 0.7 | 3.4 ± 0.2 |
| NM2ABC | 339 ± 17 | 0.35 ± 0.01 | −14.3 ± 0.3 | 43.4 ± 0.5 |
| NM3ABC | 329 ± 3 | 0.28 ± 0.01 | −45.0 ± 0.4 | 47.4 ± 2.0 |

Effective diameter ($D_{eff}$), polydispersity index (PdI) and $\zeta$-potential of nanoformulation samples diluted in water were determined by dynamic light scattering (DLS). Drug loadings of lyophilized nanoformulations were determined by HPLC.
Drug loading (%) = [entrapped drug/nanoparticles weight] × 100.
Data are expressed as mean ± SD.

Macrophage-drug interactions are demonstrated by LASER ART technologies. These have been shown to improve ART pharmacokinetics and pharmacodynamics by facilitating cell and tissue drug depots in the reticuloendothelial system (Gnanadhas, et al., J. Clin. Invest. (2017) 127:857-873; Puligujja, et al., Biomaterials (2015) 41:141-150; Edagwa, et al., Nat. Mater. (2018) 17:114-116). Macrophages are outstanding targets for LASER ART due to their large storage capacity, their high mobility that allows entry to sites of infection and inflammation, and their role as viral reservoirs (Arainga, et al., Retrovirology (2017) 14:17; Arainga, et al., Retrovirology (2015) 12:5). To affirm such observations, NM1ABC, NM2ABC and NM3ABC were administered to MDMs at concentrations of 100 µM. The intracellular prodrug concentrations were subsequently evaluated over 8 hours. As shown in FIG. 2A, the highest drug nanoparticle MDM uptake was observed with NM3ABC. At 8 hours, the intracellular prodrug concentration for NM3ABC was 118.5 nmol per $10^6$ cells, a 56- and 108-fold higher concentration than that observed for NM1ABC (2.1 nmol per $10^6$ cells) or NM2ABC (1.1 nmol per $10^6$ cells), respectively. Visualization of nanoparticles within MDMs by TEM revealed greater accumulation of NM3ABC nanoparticles in the cytoplasmic vesicles compared to NM1ABC and NM2ABC (FIG. 2E). These observations reflect nanoparticle stability (Kumar, et al., J. Controlled Release (2015) 220:141-148). To further confirm the release of ProTides from the nanoparticles and their conversion to active metabolites, the intracellular CBV-TP levels in the MDMs was quantified after a single exposure to ABC, NM1ABC, NM2ABC or NM3ABC. As shown in FIG. 2B, the CBV-TP levels for ABC increased over time and peaked at 4 hours (811 fmol per $10^6$ cells) before declining by 37% (510 fmol per $10^6$ cells) at 8 hours. For NM1ABC, the maximum CBV-TP levels were observed at 8 hours (39,533 fmol per $10^6$ cells) while NM2ABC displayed the highest CBV-TP concentration of 39,015 fmol per $10^6$ cells at 4 hours followed by a 43% decrease (22,274 fmol per $10^6$ cells) at 8 hours. Even though lower concentrations of CBV-TP were measured for NM3ABC compared to NM1ABC or NM2ABC, the active metabolite levels were sustained over 8 h, ranging from 4626 to 8601 fmol per $10^6$ cells versus 215 and 811 fmol per $10^6$ cells for ABC. Conversion of M3ABC to CBV-TP demonstrates sustained drug release and could lead to improved patient adherence to therapeutic ARVs. To explore the potential of ProTide formulations to extend the apparent half-life of ABC, MDMs were exposed to formulations for 8 hours. The intracellular ProTide and CBV-TP levels were measured over a 30-day time period. As shown in FIG. 2C, the amount of ProTide retained by MDM was undetectable for NM1ABC and NM2ABC, while NM3ABC exhibited drug concentrations of 95.3 and 48.5 nmol per $10^6$ cells at days 1 and 30, respectively. The retention of CBV-TP inMDMs (FIG. 2D) was sustained until day 30 for NM1ABC, NM2ABC and NM3ABC but only detected to day 5 for ABC. Notably, a single treatment of MDMs with NM3ABC provided steady and sustained CBV-TP levels greater than 100 fmol per $10^6$ cells over the entire 30 day period. Such sustained release formulations minimizes variant pharmacokinetic profiles and maintain effective drug concentrations at cellular and tissue reservoirs of infection.

To determine whether sustained intracellular CBV-TP from ProTide formulations would translate into improved antiretroviral activity, MDMs were challenged with HIV-$1_{ADA}$ for up to 30 days after a single 8 hour treatment with 100 µM of ABC equivalent. HIV-1 reverse transcriptase (RT) activity and p24 antigen expression were assessed in infectious supernatants and adherent MDMs on day 10 post-infection. As shown in FIGS. 3A and C, complete viral inhibition was observed for up to 15 days for NM1ABC. At day 20, 91% viral inhibition was recorded that gradually decreased to 83% inhibition at day 30. HIV-1 p24 antigen staining showed that NM2ABC protected MDM from infection with viral breakthrough at day 30. Of significance, full viral inhibition was observed for 30 days after treatment with NM3ABC. In contrast, minimal protection against viral infection was observed with native ABC at all time points. Comparisons of antiviral efficacy of NM3ABC were then assessed to determine the lowest drug concentration required for long-term MDM protection against viral infection. As shown in FIGS. 3B and D, 50 µM NM3ABC afforded complete viral inhibition for up to 30 days, while a single 8 hour treatment with 25 µM or 10 µM NM3ABC inhibited viral replication by greater than 90% at day 30 post drug treatment. These results paralleled prolonged high intracellular CBV-TP levels for NM3ABC compared to ABC, NM1ABC, or NM2ABC.

A pilot in vivo study in rats was conducted with NM3ABC. Peripheral blood mononuclear cells were recovered from whole blood and the intracellular CBV-TP levels measured at day 7 (Table 2). Reduced CBV-TP levels are explained, in part, by the rapid degradation of ProTides or slow cleavage of phosphoramide intermediates in rodents that precedes triphosphate formation (Slusarczyk, et al., J. Med. Chem. (2014) 57:1531-1542).

TABLE 2

| Time (Hours) | CBV-TP level (fmol/million cells) | |
|---|---|---|
| | Rat 1 | Rat 2 |
| 2 | 1.07 | 7.84 |
| 24 | 4.23 | 5.36 |
| 168 | 4.51 | 9.37 |

Rats were injected intramuscularly with 45 mg/kg ABC equivalents using NM3ABC. PBMC were extracted from whole blood samples collected 2, 24 and 168 hours after injection. CBV-TP level were analyzed.

In conclusion, LASER ART can overcome challenges of ARV adherence and biodistribution. M1ABC, M2ABC, and M3ABC ProTides were synthesized and NM3ABC nanoparticles exhibited improved MDM drug uptake, sustained retention and antiretroviral activities for up to one month.

Example 2

Synthesis of Abacavir (PABC), Lamivudine (P3TC), Emtricitabine (PFTC) and Tenofovir (PTFV) ProTides Synthesis of phenyl (docosanoxy-alaninyl or docosanoxy-phenylalaninyl) chlorophosphate. The compounds were synthesized as illustrated in FIG. 4.

Briefly, phenyl dichlorophosphate (1 mol) and L-alanine- or L-phenylalanine-docosanoyl ester amines (1 mol) were suspended in anhydrous dichloromethane, and cooled to −80° C. To this mixture, a pre-cooled (−80° C.) solution of anhydrous triethylamine (2 mol) in dichloromethane was added drop-wise. The reactions were stirred and gradually warmed to room temperature over 16 hours under an inert argon atmosphere. The solvent was removed under vacuum to yield colorless solids that were resuspended into diethyl ether and filtered. The filtrates were collected and dried by rotary evaporator to give colorless oils that were used in the next step without further purification.

Coupling of phenyl (docosanoxy-alaninyl or docosanoxy-phenylalaninyl) chlorophosphate with ABC, FTC, or 3TC to form PABC, PFTC, or P3TC. Covalent linkage of phenyl (docosanoxy-alaninyl or docosanoxy-phenylalaninyl) chlorophosphate to ABC, FTC, or 3TC was performed as illustrated in FIG. 4A. The parent drug(s) (1 mol) was dried by azeotroping from anhydrous pyridine, then suspended in anhydrous THF and cooled to −80° C. under argon. Tert-butylmagnesium chloride (2 mol, 1.0 M solution in THF) was added to the mixture and stirring was continued for 10 minutes. Phenyl dichlorophosphate (1 mol, solution in THF) was added drop-wise to the deprotonated parent compound (s) and the mixture was stirred for 90 hours at room temperature. The reaction mixture was then cooled to 0° C. and quenched with aqueous saturated ammonium chloride solution. The solvent was removed under vacuum, and the ProTides were isolated on a silica column chromatography. The purified PABC, PFTC, and P3TC prodrugs were characterized using mass spectrometry, HPLC, FTIR and NMR spectroscopy. FIG. 4B provides schematic structures of the compounds.

Synthesis of tenofovir (PTFV) ProTide. PTFV was synthesized as illustrated in FIG. 4A. PTFV was isolated on a silica column chromatography. The purified PTFV prodrug was characterized using mass spectrometry, HPLC, FTIR and NMR spectroscopy.

Example 3

The LASER ProTide nanocrystals (NPABC, NP3TC, NPFTC and NPTFV) may be coated with either cell or tissue receptor targeted or non-targeted poloxamer 407 (P407), poloxamer 338 (P338), 1,2-distearoyl-sn-glycero-3-phosphocholine (DSPC), 1,2-distearoyl-sn-glycero-3-phosphoethanolamine-N-carboxy(polyethylene glycol)-2000 (DSPE-PEG) or polyvinyl alcohol (PVA). The nanocrystals may also be stabilized with polysorbate and polyethylene glycol surfactants. Here, a drug to surfactant ratio of 2:1 by weight was used to manufacture NPABC nanoparticles. Briefly, 1-5% (w/v) PABC and 0.5-2.5% (w/v) P407 were mixed in sterile phosphate buffer. The premixed suspensions were nanoformulated by wet milling or high-pressure homogenization at 20,000-psi until desirable size and polydispersity index were achieved. The LASER ProTide nanoformulations were characterized for particle size, polydispersity index (PDI) and zeta potential by dynamic light scattering (DLS). This was done on a Malvern Zetasizer, Nano Series Nano-ZS (Malvern Instruments Inc, Westborough, Mass.). For P407-PABC nanoparticles (NPABC), the average size (diameter) was 350 nm, the PDI was 0.28, and the charge was −21.4 mV.

Nanoparticle morphology was determined by scanning electron microscopy (SEM). UPLC MS/MS was used for drug quantitation. The conversion of ABC to PABC facilitated production of stable nanocrystals with a drug loading capacity of more than 70%.

Example 4

Macrophage uptake and retention. Human monocytes were obtained by leukapheresis from HIV-1/2 and hepatitis B seronegative donors, and then purified by counter-current centrifugal elutriation as described (Balkundi, et al., Intl. J. Nanomed. (2011) 6:3393-3404; Nowacek, et al., Nanomed. (2009) 4(8):903-917). Human monocytes were plated in a 12-well plate at a density of $1.0 \times 10^6$ cells per well using DMEM supplemented with 10% heat-inactivated pooled human serum, 1% glutamine, 10 µg/mL ciprofloxacin, and 50 µg/mL gentamicin. Cells were maintained at 37° C. in a 5% $CO_2$ incubator. After 7 days of differentiation in the presence of 1000 U/mL recombinant human macrophage colony stimulating factor (MCSF), MDM were treated with 100 µM ABC, nanoformulated myristoylated ABC (NMABC; described in PCT/US15/54826), or NPABC. Uptake of drug was assessed by measurements of intracellular drug concentrations at 1, 2, 4 and 8 hours after treatment. For drug retention studies, cells were treated for 8 hours then washed with PBS and maintained with half-media changes every other day until collection at days 1, 5, 10, 15 and 20. For both studies, adherent MDM were washed with PBS, then scraped into PBS, and counted at indicated time points using an Invitrogen Countess Automated Cell Counter (Carlsbad, Calif.). Cells were pelleted by centrifugation at 3,000 rpm for 8 minutes at 4° C. Cell pellets were briefly sonicated in 200 µL methanol to extract drug and centrifuged at 14,000 rpm for 10 minutes at 4° C. to pellet cell debris. Drug content was determined by UPLC-UV/Vis.

Antiretroviral activities. Antiretroviral efficacy was determined by measurements of HIV reverse transcriptase (RT) activity. For $IC_{50}$ determination, MDM were exposed to various concentrations (0.01-1000 nM) of ABC, MABC or PABC for 1 hour followed by challenge with HIV-$1_{ADA}$ at a multiplicity of infection (MOI) of 0.1 infectious particles per cell for 4 hours. Following viral challenge, cells were washed and incubated with the same concentration of drug used before infection for an additional 10 days in culture. Culture fluids were collected on day 10 for the measurement of RT activity. To assess antiretroviral efficacy, MDM were treated with 100 µM ABC, PABC or NPABC as described above for 8 hours. After treatment, cells were washed with PBS and cultured with fresh media, with half-media exchanges every other day. At 0, 4, 12 hours, and 1, 5, 10, 15 or 20 days after treatment, cells were challenged with HIV-$1_{ADA}$ at an MOI of 0.1 infectious particles per cell for 16 hours. After viral infection, the cells were cultured an additional 10 days with half-media exchanges every other day. Culture fluids were collected for measurement of RT activity. Cells were fixed with 4% PFA and expression of HIV-1 p24 antigen was determined by immunocytochemistry.

Conversion of ABC into more hydrophobic and lipophilic PABC and encasement into NPABC nanoparticles significantly improved the potency and intracellular accumulation of the drug compared to ABC or nanoformulated myristoylated ABC (NMABC). The PABC nanoformulations were easily taken up by human monocyte derived macrophages (MDM) with sustained drug release up to 20 days measurement period, whereas the parent drug or myristoylated prodrug formulations (NMABC) were eliminated from MDM within a day or 15 days of treatment, respectively (FIG. 5).

Significant improvements in MDM antiretroviral efficacy were also observed for PABC and NPABC. Notably, MDM treated with PABC or NPABC exhibited enhanced antiretroviral activity compared to ABC. HIV-1 p24 was not detected in the PABC or NPABC-treated groups at the measured timepoints (FIG. 6). Briefly, MDM were treated with 100 µM native ABC, PABC, or NPABC for 8 hours. After 1, 5, 10, 15 or 20 days, MDM were challenged with HIV-$1_{ADA}$ at a multiplicity of infection (MOI) of 0.1 for 16 hours. Uninfected cells without treatment served as negative controls. HIV-1-infected cells without treatment served as positive controls. All samples were collected 10 days after viral challenge for RT assay and HIV-1 p24 staining.

Example 5

NP3TC nanoparticles were also prepared and studied as described for NPABC nanoparticles in Examples 2-4. At the outset, MDM cells remained viable in MTT assays upon exposure to P3TC after 24 hours at a drug concentration of 200 µM, thereby demonstrating a lack of toxicity with the compound. The uptake and retention of native drug 3TC and nanoformulated 3TC prodrug (NP3TC) in MDM was also determined. These were measured starting with equal drug concentrations for all tested formulations (100 µM). Uptake of drug was assessed by measurements of intracellular drug concentrations at 2, 4, 8, and 24 hours after treatment. For drug retention studies, cells were treated for 8 hours then washed with PBS and maintained with half-media changes every other day until collection at days 1, 5, 10, 15, 20, 25, and 30. As seen in FIGS. 7A and 7B, NP3TC was taken up by MDM more readily and retained longer than 3TC alone. Additionally, 3TC triphosphate levels were measured. As seen in FIG. 7C, 3TC triphosphate levels were detected more rapidly and to a higher level in MDM treated with NP3TC than 3TC. Moreover, as seen in FIG. 7D, 3TC triphosphate levels remained higher and for a longer period of time in MDM treated with NP3TC than 3TC. Intracellular drug concentrations and 3TC-TP levels were determined by UPLC-MS/MS.

Significant improvements in MDM antiretroviral efficacy were also observed for NP3TC compared to 3TC in terms of inhibiting RT activity and HIV-1 replication (FIG. 8). Notably, MDM treated with NP3TC exhibited enhanced antiretroviral activity compared to 3TC. Significant HIV-1 p24 was not detected in the NP3TC-treated groups at the measured timepoints (FIG. 8B). Briefly, MDM were treated with 100 µM native 3TC or NP3TC for 8 hours. After 1, 5, 10, 15, 20, or 30 days, MDM were challenged with HIV-$1_{ADA}$ at a multiplicity of infection (MOI) of 0.1 for 16 hours. After viral infection, the cells were cultured an additional 10 days with half-media exchanges every other day. Culture fluids were collected for measurement of RT activity (FIG. 8A). Cells were fixed with 4% PFA and expression of HIV-1 p24 antigen was determined by immunocytochemistry. Uninfected cells without treatment served as negative controls. HIV-1-infected cells without treatment served as positive controls.

Sprague Dawley rats were administered a single 75 mg/kg intramuscular (IM) dose of NP3TC or 3TC. Drug concentrations were later quantified by LC-MS/MS. P3TC was observed in various tissues (e.g., spleen, liver, and lymph nodes) of the rats treated with a single IM dose of NP3TC, but not 3TC. As seen in FIG. 9, P3TC was also observed in the blood 28 days after injection of NP3TC.

Example 6

NPFTC nanoparticles were also prepared and studied as described for above in Examples 2-4.

The uptake and retention of native drug FTC and nanoformulated FTC prodrug (NPFTC) in MDM was determined. These were measured starting with equal drug concentrations for all tested formulations (100 µM). Uptake of drug was assessed by measurements of intracellular FTC triphosphate concentrations at 2, 4, and 8 hours after treatment. For drug retention studies, cells were treated for 8 hours then washed with PBS and maintained with half-media changes every other day until collection at days 1, 5, 10, 20, and 30. As seen in FIG. 10A, FTC triphosphate levels were detected more rapidly and to a higher level in MDM treated with NPFTC than FTC. Moreover, as seen in FIG. 10B, FTC triphosphate levels remained higher and for a longer period of time in MDM treated with NPFTC than FTC. Intracellular drug concentrations and 3TC-TP levels were determined by UPLC-MS/MS.

Significant improvements in MDM antiretroviral efficacy were also observed for NPFTC compared to FTC in terms of inhibiting HIV-1 replication (FIG. 10C). Notably, MDM treated with NPFTC exhibited enhanced antiretroviral activity compared to FTC. Significant HIV-1 p24 was not detected in the NPFTC-treated groups at the measured timepoints (FIG. 10C). Briefly, MDM were treated with 100 µM native FTC or NPFTC for 8 hours. After 1, 5, 10, 15, 20, or 30 days, MDM were challenged with HIV-$1_{ADA}$ at a multiplicity of infection (MOI) of 0.1 for 16 hours. After viral infection, the cells were cultured an additional 10 days with half-media exchanges every other day. Cells were fixed with 4% PFA and expression of HIV-1 p24 antigen was determined by immunocytochemistry. Uninfected cells without treatment served as negative controls. HIV-1-infected cells without treatment served as positive controls.

Sprague Dawley rats were administered a single 45 mg/kg intramuscular (IM) dose of NPFTC or FTC. Drug concentrations were later quantified by LC-MS/MS. As seen in FIG. 11, significantly more drug was detected in the blood, spleen, and lymph nodes of rats treated with NPFTC compared to FTC.

A number of publications and patent documents are cited throughout the foregoing specification in order to describe the state of the art to which this invention pertains. The entire disclosure of each of these citations is incorporated by reference herein.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A compound represented by:

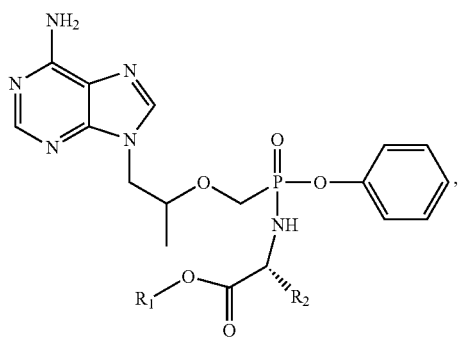

wherein:
$R_1$ is C18-C24 unsaturated or saturated aliphatic group, optionally substituted with at least one heteroatom; and
$R_2$ is an amino acid side chain.

2. The prodrug of claim 1, wherein $R_1$ is an alkyl chain of a fatty acid.

3. The prodrug of claim 1, wherein $R_1$ is docosyl.

4. The prodrug of claim 1, wherein $R_2$ is selected from the group consisting of H, phenyl, $CH_3$, —$CH_2iPr$, —$CH_2Ph$, and —$CH_2PhOH$.

5. The compound of claim 1, wherein said compound is selected from the group consisting of:

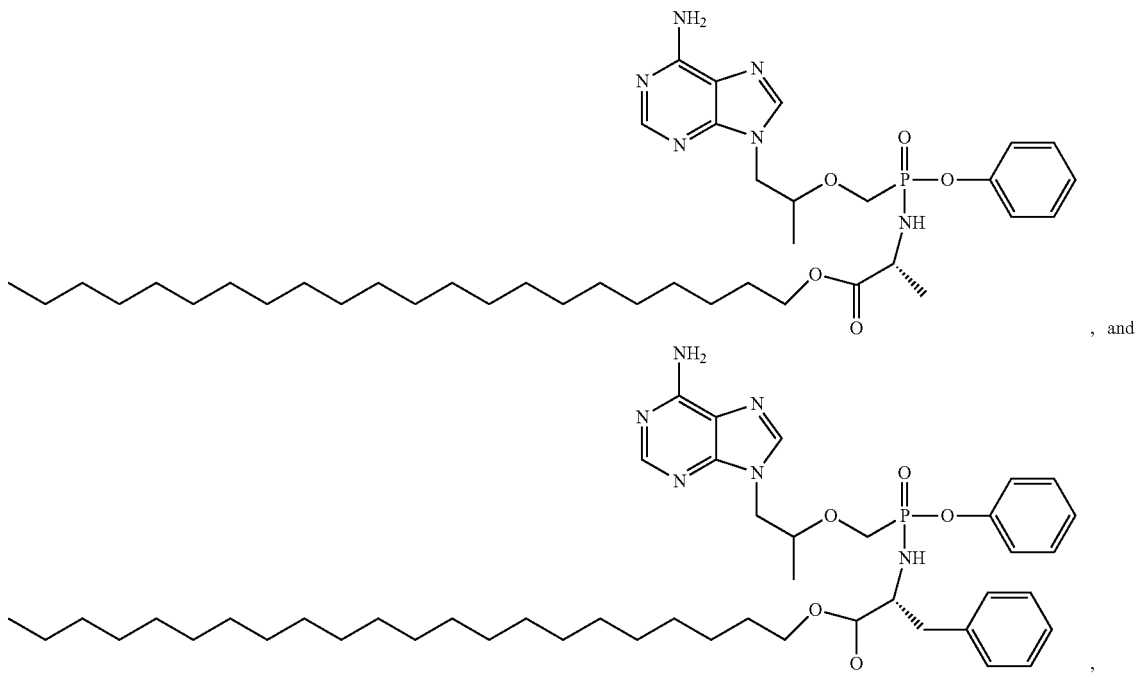

and pharmaceutically acceptable salts thereof.

6. A nanoparticle comprising at least one compound of claim 1, or a pharmaceutically acceptable salt thereof, and at least one polymer or surfactant.

7. The nanoparticle of claim 6, wherein said compound is crystalline.

8. The nanoparticle of claim 6, wherein said polymer or surfactant is an amphiphilic block copolymer.

9. The nanoparticle of claim 8, wherein said amphiphilic block copolymer comprises at least one block of poly(oxyethylene) and at least one block of poly(oxypropylene).

10. The nanoparticle of claim 8, wherein the polymer or surfactant is P407.

11. The nanoparticle of claim 6, wherein said nanoparticle further comprises a polymer or surfactant linked to at least one targeting ligand.

12. The nanoparticle of claim 6, wherein the diameter of the nanoparticle is about 100 nm to 1 μm.

13. A composition comprising at least one nanoparticle of claim 6 and at least one pharmaceutically acceptable carrier.

14. A composition comprising at least one compound of claim 1, or a pharmaceutically acceptable salt thereof, and at least one pharmaceutically acceptable carrier.

15. A method for treating, inhibiting, and/or preventing a disease or disorder in a subject in need thereof, said method comprising administering to said subject a compound of claim 1, or a pharmaceutically acceptable salt thereof, wherein the disease or disorder is cancer, viral infection, or a clotting disorder.

16. The method of claim 15, wherein the disease or disorder is a viral infection.

17. The method of claim 16, wherein the viral infection is an HIV, hepatitis B, hepatitis C, influenza A, influenza B, herpes simplex, or Ebola infection.

18. The compound of claim 1, wherein $R_2$ is a side chain of phenylalanine, alanine, leucine, or tyrosine.

\* \* \* \* \*